US007998738B2

(12) United States Patent
Arnaout

(10) Patent No.: US 7,998,738 B2
(45) Date of Patent: Aug. 16, 2011

(54) INTEGRIN-BINDING ANTIBODIES

(75) Inventor: M. Amin Arnaout, Chestnut Hill, MA (US)

(73) Assignee: The General Hospital Corporation, Boston, MA (US)

( * ) Notice: Subject to any disclaimer, the term of this patent is extended or adjusted under 35 U.S.C. 154(b) by 75 days.

(21) Appl. No.: 12/021,074

(22) Filed: Jan. 28, 2008

(65) Prior Publication Data

US 2009/0023226 A1    Jan. 22, 2009

Related U.S. Application Data

(63) Continuation of application No. 10/144,259, filed on May 10, 2002, now Pat. No. 7,323,552.

(51) Int. Cl.
*C12N 5/20* (2006.01)
*C07K 16/00* (2006.01)
*C07K 16/28* (2006.01)

(52) U.S. Cl. .............. 435/326; 530/387.1; 530/388.1; 530/388.22

(58) Field of Classification Search .......... None
See application file for complete search history.

(56) References Cited

U.S. PATENT DOCUMENTS

| 5,985,278 | A | 11/1999 | Mitjans et al. | |
| 7,064,180 | B2* | 6/2006 | Arnaout et al. | 530/324 |
| 7,323,552 | B2* | 1/2008 | Arnaout et al. | 530/402 |
| 2003/0078375 | A1 | 4/2003 | Arnaout et al. | |

FOREIGN PATENT DOCUMENTS

| WO | WO00/59878 | 10/2000 |
| WO | WO00/60355 | 10/2000 |
| WO | WO02/04521 | 1/2002 |
| WO | WO02/09737 | 2/2002 |
| WO | WO02/31511 | 4/2002 |

OTHER PUBLICATIONS

Rieu et al. The A-domain of beta 2 integrin CR3 (CD11b/CD18) is a receptor for the hookworm-derived neutrophil adhesion inhibitor NIF.. J Cell Biol. Dec. 1994;127(6 Pt 2):2081-91.*
Li et al., The Journal of Immunology, 2002;168;1219-1225.
Baldwin et al., "Cation binding to the integrin CD11b I domain and activation model assessment", *Structure*, 6:923-935 (1998).
Burgess et al., "Possible dissociation of the Heparin-Binding and Mitogenic Activities" J. Cell Biol III: 2129-2138 (1990).
Edwards et al., "Mapping the Intercellular Adhesion Molecule-1 and—2 Binding Site on the Inserted Domain of Leukocyte Function-associated Antigen-1", *The Journal of Biological Chemistry*, 273:28937-28944 (1998).
Emsley et al., "Structural Basis of Collagen Recognition by Integrin α2β1", *Cell*, 100:47-56 (2000).
Emsley et al., "Crystal Structure of the I Domain from Integrin α2β1", *The Jounal of Biological Chemistry*, 272:28512-28517 (1997).

Feng et al., "Peptides Derived from the Complementarity-determining Regions of Anti-Mac-1 Antibodies Block Intercellular Adhesion Molecule-1 Interaction with Mac-1", *The Jounal of Biological Chemistry*, 273:5625-5630 (1998).
Kamata T and Takada Y, "Direct Binding of Collagen to the I Domain of Integrin α2β1 (VLA-2, CD49b/CD29) in a Divalent Cation-independent Manner", *The Journal of Biolocal Chemistry*, 269:26006-26010 (1994).
Huth et al., "NMR and Mutagenesis Evidence for and I Domain Allosteric Site . . . "Proc. Nat'l. Acad. Sci. 97(10):5235, 2000.
Kern et al., "The Role of the I Domain in Ligand Binding of the Human Integrin $\alpha_1\beta_1$", *The Journal of Biological Chemistry*, 269:22811-22816 (1994).
Lazar et al., "Transforming Growth Factor Alpha . . . " Mol. Cell. Biol. 8:1247-1252 (1988).
Lee et al., "Crystal Structure of the A Domain from the α Subunit of Integrin CR3 (CD11b/CD18)" *Cell*, 80:631-638 (1995).
Lee et al., "Two conformations of the integrin A-domain (I-domain): a pathway for activation?", *Structure*, 3:1333-1340 (1995).
Legge et al., "NMR Solution Structure of the Inserted Domain of Human Leukocyte Function Associated Antigen-1", *Journal of Molecular Biology*, 295:1251-1264 (2000).
Li et al., "Two Functional States of the CD11b A-Domain: Correlations with Key Features of Two $Mn^{2+}$—complexed Crystal Structures", *The Journal of Cell Biology*, 143:1523-1534 (1998).
Michishita et al., "A Novel Divalent Cation-Binding Site in the A Domain of the β2 Integrin CR3 (CD1 1b/CD18) Is Essential for Ligand Binding", *Cell*, 72:857-867 (1993).
Nolte et al., "Crystal structure of the α1β1 integrin I-domain: insights into Integrin I-domain function", *FEBS Letters*, 452:379-385 (1999).
Oxvig et al., "Conformational changes in tertiary structure near the ligand binding site of an integrin I domain", *Proc. Natl. Acad. Sci. USA*, 96:2215-2220 (1999).
Rieu et al., "Solvent-accessible Residues on the Metal Ion-dependent Adhesion Site Face on Integrin CR3 Mediate Its binding to the Netrophil Inhibitory Factor", *The Journal of Biological Chemistry*,271:15858-15861 (1996).
Smith JW and Cheresh DA, "The Arg-Cly-Asp Binding Domain of the Vitronectin Receptor", *The Journal of Biological Chemistry*, 263:18726-18731 (1988).
Xiong et al., "An Isoleucine-based Allosteric Switch Controls Affinity . . . " J. of Biol. Chem. 275:38762-38767, 2000.
Zhang L and Plow EF, "A Discrete Site Modulates Activation of I Domains", *The Journal of Biological Chemistry*, 271:29953-29957 (1996).
Zhang L and Plow EF, "Amino Acid Sequences within the αSubunit of Integrin $\alpha_M\beta_2$ (Mac-1) Critical for Specific Recognition of C3bi", *Biochemistry*, 38:8064-8071 (1999).

* cited by examiner

*Primary Examiner* — Maher Haddad
(74) *Attorney, Agent, or Firm* — Fish & Richardson P.C.

(57) ABSTRACT

Ligand-mimetic monoclonal antibody mAb 107, produced by a hybridoma cell line deposited in the American Type Culture Collection under Accession Number ATCC PTA-11614, which binds to CD11b MIDAS in an activation-independent manner.

5 Claims, 15 Drawing Sheets

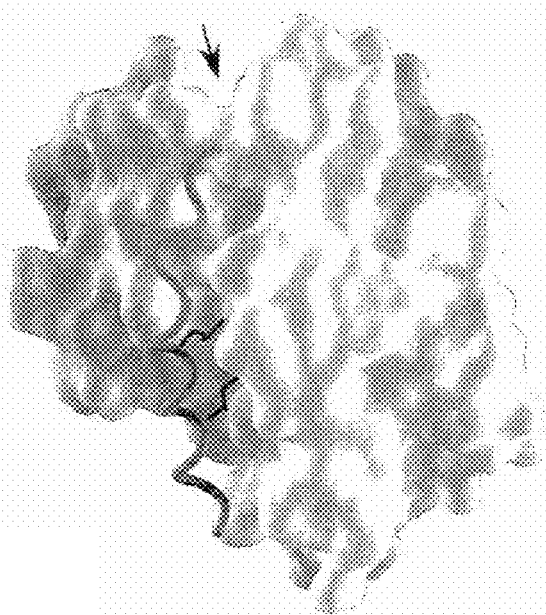
FIG. 1A  FIG. 1B
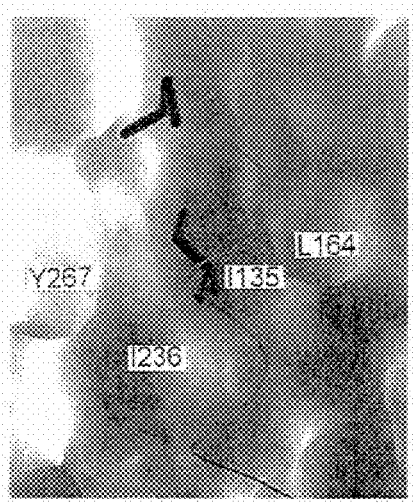
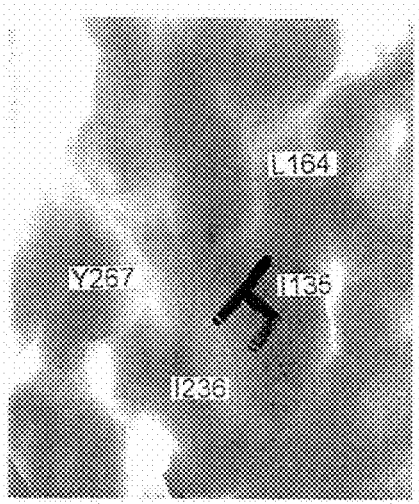
FIG. 1C  FIG. 1D

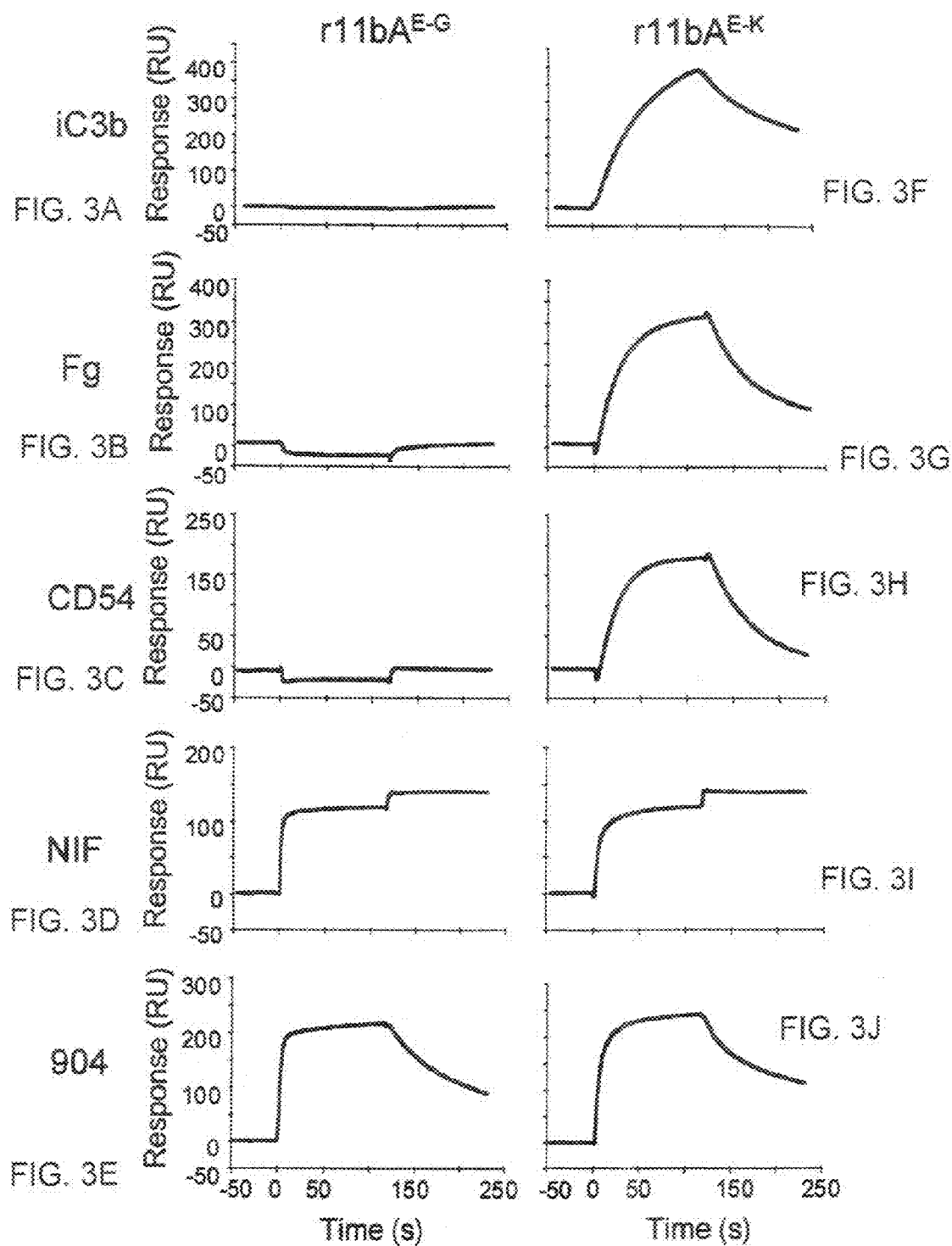

```
CD11b    FEALKTIQNQ  LREKIFAIEG TQTGSSSSFE  HEMSQEGFSA AIT
CD11c    FDALKDIQNQ  LKEKIFAIEG TETTSSSSFE  LEMAQEGFSA VFT
CD11d    FAALGSIQKQ  LQEKIYAVEG TQSRASSSFQ  HEMSQEGFST ALT
CD11a    FEKLKDLFTE  LQKKIYVIEG TSKQDLTSFN  MELSSSGISA DLS
α11      EAALKDIVDA  LGDRIFSLEG TNKNE-TSFG  LEMSQTGFSS HVV
α10      EAALTDIVDA  LGDRIFGLEG SHAENESSFG  LEMSQIGFST HRL
α1       ELALVTIVKT  LGERIFALEA TADQSAASFE  MEMSQTGFSA HYS
α2       EAALLEKAGT  LGEQIFSIEG TVQGG-DNFQ  MEMSQVGFSA DYS
αE       YMALDGLLSK  LRYNIISMEG TVGDA---LH  YQLAQIGFSA QIL
         ─────────────────────              ───────────
              α7 helix                         Cup   A4
```

FIG. 9

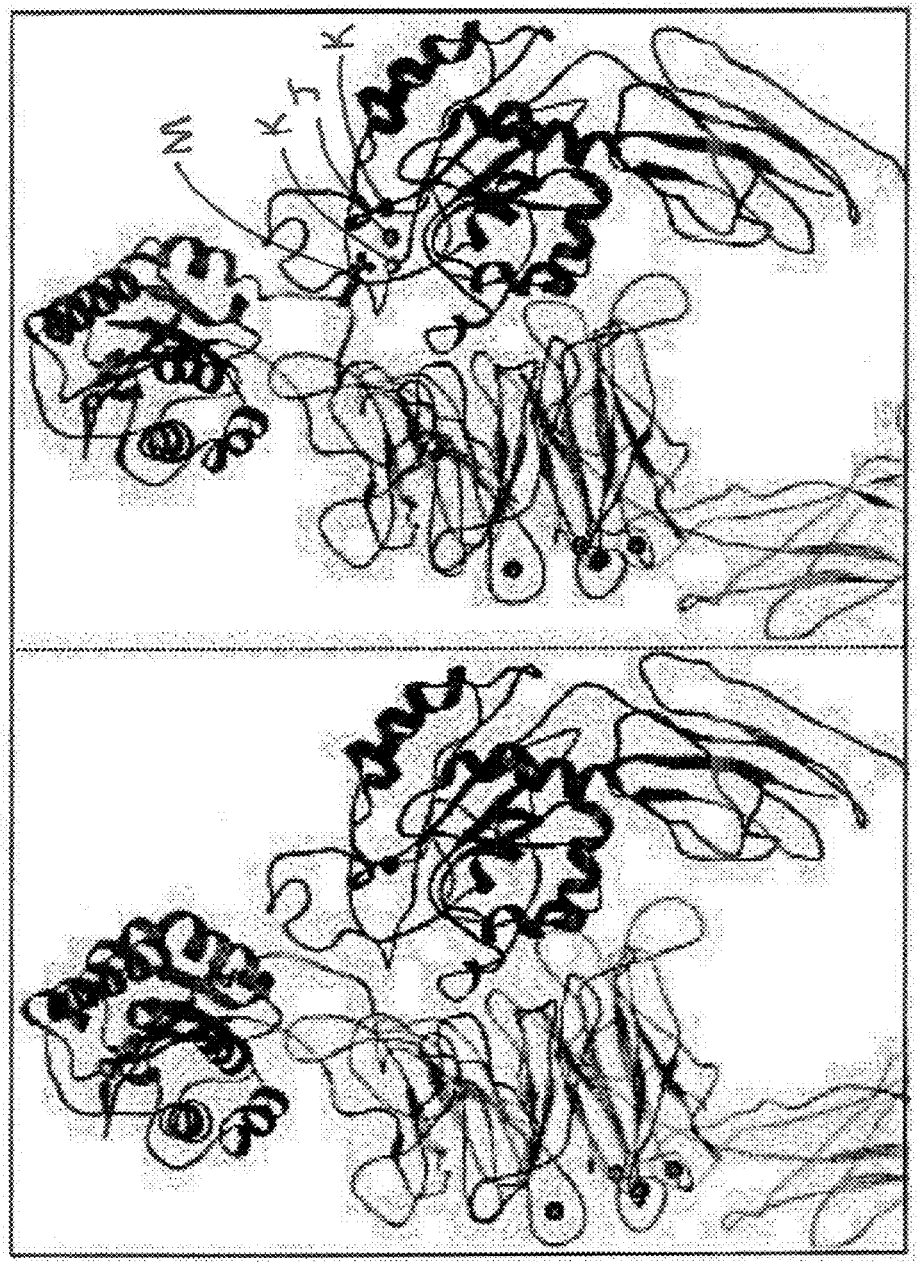

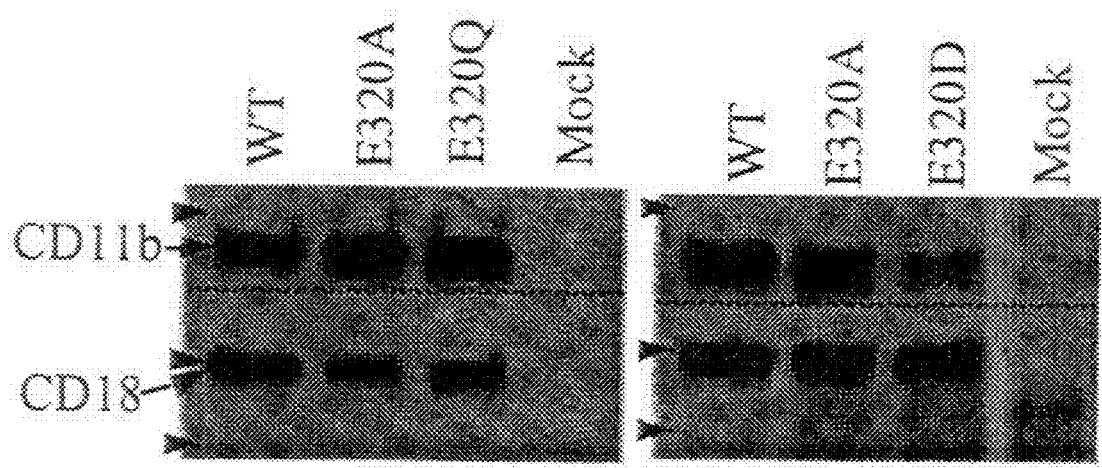
FIG. 11A     FIG. 11B

FIG. 11C
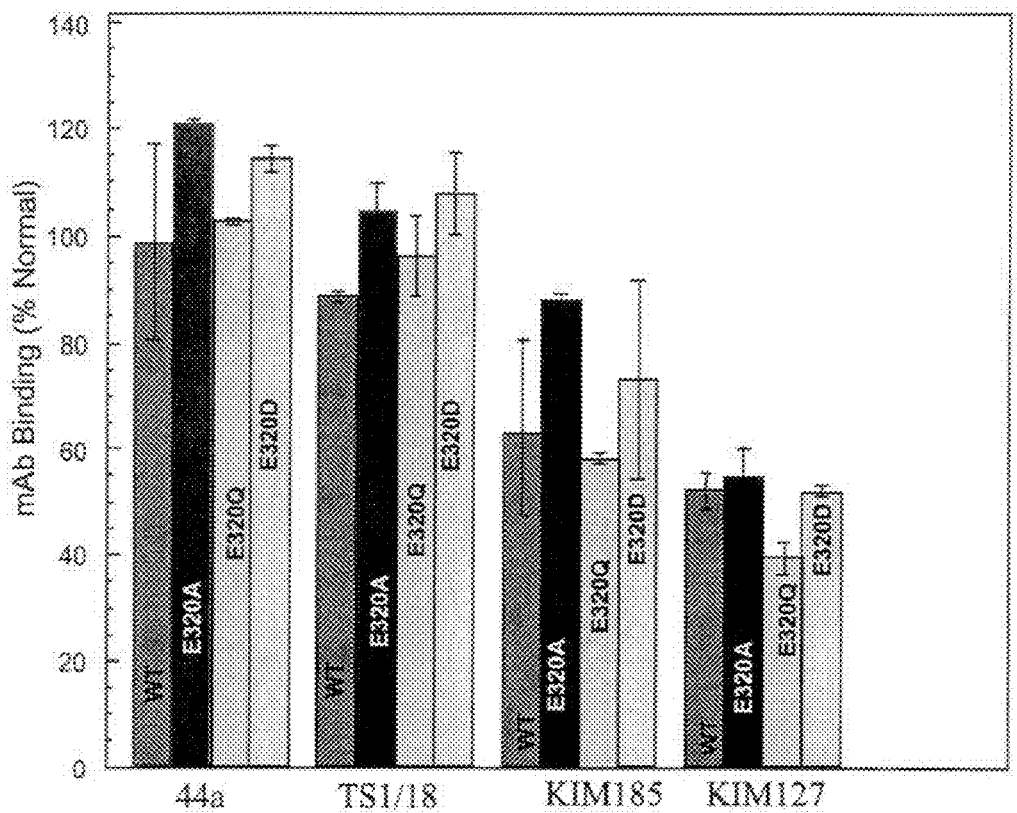
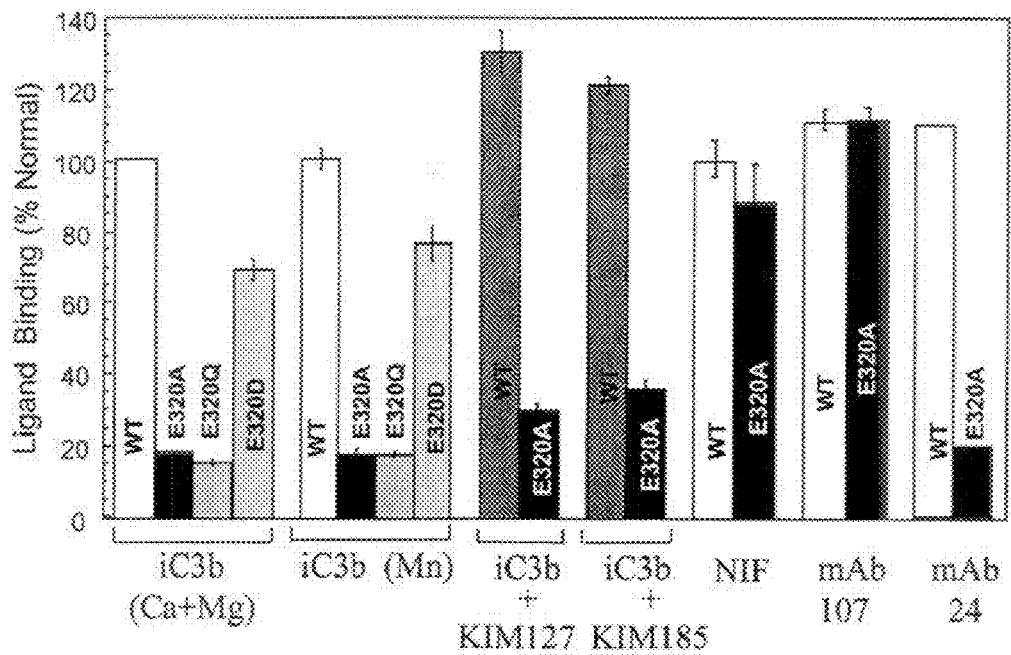
FIG. 11D

```
   1  malrvlllta ltlchgfnld tenamtfqen argfgqsvvq lqgsrvvvga pqeivaanqr
  61  gslyqcdyst gscepirlqv pveavnmslg lslaattspp qllacgptvh qtcsentyvk
 121  glcflfgsnl rqqpqkfpea lrgcpqedsd iaflidgsgs iiphdfrrmk efvstvmeql
 181  kksktlfslm qyseefrihf tfkefqnnpn prslvkpitq llgrthtatg irkvvrelfn
 241  itngarknaf kilvvitdge kfgdplgyed vipeadregv iryvigvgda frseksrqel
 301  ntiaskpprd hvfqvnnfea lktiqnqlre kifaiegtqt gssssfehem sqegfsaait
 361  sngpllstvg sydwaggvfl ytskekstfi nmtrvdsdmn daylgyaaai ilmrvqslv
 421  lgapryqhig lvamfrqntg mwesnanvkg tqigayfgas lcsvdvdsng stdlvligap
 481  hyyeqtrggq vsvcplprgq rarwqcdavl ygeqgqpwgr fgaaltvlgd vngdkltdva
 541  igapgeednr gavylfhgts gsgispshsq riagsklspr lqyfgqslsg gqdltmdglv
 601  dltvgaqghv lllrsqpvlr vkaimefnpr evamvfecn dqvvkgkeag evrvclhvqk
 661  strdrlregq iqsvvtydla ldsgrphsra vfnetknstr rqtqvlgltq tcetlklqlp
 721  nciedpvspi vlrlnfslvg tplsafgnlr pvlaedaqrl ftalfpfekn cgndnicqdd
 781  lsitfsfmsl dclvvggpre fnvtvtvmd gedsyrtqvt ffpldlsyr kvstlqnqrs
 841  qrswrlaces asstevsgal kstscsinhp ifpensevtf nitfdvdska slgnklllka
 901  nvtsenmmpr tnktefqlel pvkyavymvv tshgvstkyl nftasentsr vmqhqyqvsn
 961  lgqrslpisl vflvpvrlnq tviwdrpqvt fsenlsstch tkerlpshsd flaelrkapv
1021  vncsiavcqr iqcdipffgi qeefnatlkg nlsfdwyikt shnhllivst acilfndsvf
1081  tllpgqgafv rsqtetkvep fevpnplpli vgssvgglll lalitaalyk lgffkrqykd
1141  mmseggppga epq
```

FIG. 12

SEQUENCE LISTING

<160> NUMBER OF SEQ ID NOS: 30

<210> SEQ ID NO 1
<211> LENGTH: 191
<212> TYPE: PRT
<213> ORGANISM: Homo sapiens

<400> SEQUENCE: 1

```
Cys Pro Gln Glu Asp Ser Asp Ile Ala Phe Leu Ile Asp Gly Ser Gly
 1               5                  10                  15

Ser Ile Ile Pro His Asp Phe Arg Arg Met Lys Glu Phe Val Ser Thr
            20                  25                  30

Val Met Glu Gln Leu Lys Lys Ser Lys Thr Leu Phe Ser Leu Met Gln
        35                  40                  45

Tyr Ser Glu Glu Phe Arg Ile His Phe Thr Phe Lys Glu Phe Gln Asn
    50                  55                  60

Asn Pro Asn Pro Arg Ser Leu Val Lys Pro Ile Thr Gln Leu Leu Gly
65                  70                  75                  80

Arg Thr His Thr Ala Thr Gly Ile Arg Lys Val Val Arg Glu Leu Phe
                85                  90                  95

Asn Ile Thr Asn Gly Ala Arg Lys Asn Ala Phe Lys Ile Leu Val Val
            100                 105                 110

Ile Thr Asp Gly Glu Lys Phe Gly Asp Pro Leu Gly Tyr Glu Asp Val
        115                 120                 125

Ile Pro Glu Ala Asp Arg Glu Gly Val Ile Arg Tyr Val Ile Gly Val
    130                 135                 140

Gly Asp Ala Phe Arg Ser Glu Lys Ser Arg Gln Glu Leu Asn Thr Ile
145                 150                 155                 160

Ala Ser Lys Pro Pro Arg Asp His Val Phe Gln Val Asn Asn Phe Glu
                165                 170                 175

Ala Leu Lys Thr Ile Gln Asn Gln Leu Arg Glu Lys Ile Phe Ala
            180                 185                 190
```

<210> SEQ ID NO 2
<211> LENGTH: 191
<212> TYPE: PRT
<213> ORGANISM: Homo sapiens

<400> SEQUENCE: 2

```
Cys Pro Arg Gln Glu Gln Asp Ile Val Phe Leu Ile Asp Gly Ser Gly
 1               5                  10                  15

Ser Ile Ser Ser Arg Asn Phe Ala Thr Met Met Asn Phe Val Arg Ala
            20                  25                  30

Val Ile Ser Gln Phe Gln Arg Pro Ser Thr Gln Phe Ser Leu Met Gln
        35                  40                  45

Phe Ser Asn Lys Phe Gln Thr His Phe Thr Phe Glu Glu Phe Arg Arg
    50                  55                  60

Thr Ser Asn Pro Leu Ser Leu Leu Ala Ser Val His Gln Leu Gln Gly
65                  70                  75                  80

Phe Thr Tyr Thr Ala Thr Ala Ile Gln Asn Val Val His Arg Leu Phe
                85                  90                  95

His Ala Ser Tyr Gly Ala Arg Arg Asp Ala Thr Lys Ile Leu Ile Val
            100                 105                 110

Ile Thr Asp Gly Lys Lys Glu Gly Asp Ser Leu Asp Tyr Lys Asp Val
        115                 120                 125
```

```
Ile Pro Met Ala Asp Ala Ala Gly Ile Ile Arg Tyr Ala Ile Gly Val
        130                 135                 140

Gly Leu Ala Phe Gln Asn Arg Asn Ser Trp Lys Glu Leu Asn Asp Ile
145                 150                 155                 160

Ala Ser Lys Pro Ser Gln Glu His Ile Phe Lys Val Glu Asp Phe Asp
                165                 170                 175

Ala Leu Lys Asp Ile Gln Asn Gln Leu Lys Glu Lys Ile Phe Ala
                180                 185                 190

<210> SEQ ID NO 3
<211> LENGTH: 191
<212> TYPE: PRT
<213> ORGANISM: Homo sapiens

<400> SEQUENCE: 3

Cys Pro His Gln Glu Met Asp Ile Val Phe Leu Ile Asp Gly Ser Gly
  1               5                  10                  15

Ser Ile Asp Gln Asn Asp Phe Asn Gln Met Lys Gly Phe Val Gln Ala
                 20                  25                  30

Val Met Gly Gln Phe Glu Gly Thr Asp Thr Leu Phe Ala Leu Met Gln
             35                  40                  45

Tyr Ser Asn Leu Leu Lys Ile His Phe Thr Phe Thr Gln Phe Arg Thr
 50                  55                  60

Ser Pro Ser Gln Gln Ser Leu Val Asp Pro Ile Val Gln Leu Lys Gly
 65                  70                  75                  80

Leu Thr Phe Thr Ala Thr Gly Ile Leu Thr Val Val Thr Gln Leu Phe
                 85                  90                  95

His His Lys Asn Gly Ala Arg Lys Ser Ala Lys Lys Ile Leu Ile Val
            100                 105                 110

Ile Thr Asp Gly Gln Lys Tyr Lys Asp Pro Leu Glu Tyr Ser Asp Val
        115                 120                 125

Ile Pro Gln Ala Glu Lys Ala Gly Ile Ile Arg Tyr Ala Ile Gly Val
        130                 135                 140

Gly His Ala Phe Gln Gly Pro Thr Ala Arg Gln Glu Leu Asn Thr Ile
145                 150                 155                 160

Ser Ser Ala Pro Pro Gln Asp His Val Phe Lys Val Asp Asn Phe Ala
                165                 170                 175

Ala Leu Gly Ser Ile Gln Lys Gln Leu Gln Glu Lys Ile Tyr Ala
                180                 185                 190

<210> SEQ ID NO 4
<211> LENGTH: 184
<212> TYPE: PRT
<213> ORGANISM: Homo sapiens

<400> SEQUENCE: 4

Cys Ile Lys Gly Asn Val Asp Leu Val Phe Leu Phe Asp Gly Ser Met
  1               5                  10                  15

Ser Leu Gln Pro Asp Glu Phe Gln Lys Ile Leu Asp Phe Met Lys Asp
                 20                  25                  30

Val Met Lys Lys Leu Ser Asn Thr Ser Tyr Gln Phe Ala Ala Val Gln
             35                  40                  45

Phe Ser Thr Ser Tyr Lys Thr Glu Phe Asp Phe Ser Asp Tyr Val Lys
 50                  55                  60

Trp Lys Asp Pro Asp Ala Leu Leu Lys His Val Lys His Met Leu Leu
 65                  70                  75                  80

Leu Thr Asn Thr Phe Gly Ala Ile Asn Tyr Val Ala Thr Glu Val Phe
```

```
                    85                  90                  95
Arg Glu Glu Leu Gly Ala Arg Pro Asp Ala Thr Lys Val Leu Ile Ile
            100                 105                 110

Ile Thr Asp Gly Glu Ala Thr Asp Ser Gly Asn Ile Asp Ala Ala Lys
        115                 120                 125

Asp Ile Ile Arg Tyr Ile Ile Gly Ile Gly Lys His Phe Gln Thr Lys
    130                 135                 140

Glu Ser Gln Glu Thr Leu His Lys Phe Ala Ser Lys Pro Ala Ser Glu
145                 150                 155                 160

Phe Val Lys Ile Leu Asp Thr Phe Glu Lys Leu Lys Asp Leu Phe Thr
                165                 170                 175

Glu Leu Gln Lys Lys Ile Tyr Val
            180

<210> SEQ ID NO 5
<211> LENGTH: 195
<212> TYPE: PRT
<213> ORGANISM: Homo sapiens

<400> SEQUENCE: 5

Cys Ser Thr Gln Leu Asp Ile Val Ile Val Leu Asp Gly Ser Asn Ser
1               5                   10                  15

Ile Tyr Pro Trp Asp Ser Val Thr Ala Phe Leu Asn Asp Leu Leu Lys
            20                  25                  30

Arg Met Asp Ile Gly Pro Lys Gln Thr Gln Val Gly Ile Val Gln Tyr
        35                  40                  45

Gly Glu Asn Val Thr His Glu Phe Asn Leu Asn Lys Tyr Ser Ser Thr
    50                  55                  60

Glu Glu Val Leu Val Ala Ala Lys Lys Ile Val Gln Arg Gly Gly Arg
65                  70                  75                  80

Gln Thr Met Thr Ala Leu Gly Thr Asp Thr Ala Arg Lys Glu Ala Phe
                85                  90                  95

Thr Glu Ala Arg Gly Ala Arg Arg Gly Val Lys Lys Val Met Val Ile
            100                 105                 110

Val Thr Asp Gly Glu Ser His Asp Asn His Arg Leu Lys Lys Val Ile
        115                 120                 125

Gln Asp Cys Glu Asp Glu Asn Ile Gln Arg Phe Ser Ile Ala Ile Leu
    130                 135                 140

Gly Ser Tyr Asn Arg Gly Asn Leu Ser Thr Glu Lys Phe Val Glu Glu
145                 150                 155                 160

Ile Lys Ser Ile Ala Ser Glu Pro Thr Glu Lys His Phe Phe Asn Val
                165                 170                 175

Ser Asp Glu Leu Ala Leu Val Thr Ile Val Lys Thr Leu Gly Glu Arg
            180                 185                 190

Ile Phe Ala
        195

<210> SEQ ID NO 6
<211> LENGTH: 195
<212> TYPE: PRT
213> ORGANISM: Homo sapiens

<400> SEQUENCE: 6

Cys Pro Ser Leu Ile Asp Val Val Val Cys Asp Glu Ser Asn Ser
1               5                   10                  15

Ile Tyr Pro Trp Asp Ala Val Lys Asn Phe Leu Glu Lys Phe Val Gln
            20                  25                  30
```

Gly Leu Asp Ile Gly Pro Thr Lys Thr Gln Val Gly Leu Ile Gln Tyr
        35                  40                  45

Ala Asn Asn Pro Arg Val Val Phe Asn Leu Asn Thr Tyr Lys Thr Lys
 50                  55                  60

Glu Glu Met Ile Val Ala Thr Ser Gln Thr Ser Gln Tyr Gly Gly Asp
 65                  70                  75                  80

Leu Thr Asn Thr Phe Gly Ala Ile Gln Tyr Ala Arg Lys Tyr Ala Tyr
                 85                  90                  95

Ser Ala Ala Ser Gly Gly Arg Arg Ser Ala Thr Lys Val Met Val Val
                100                 105                 110

Val Thr Asp Gly Glu Ser His Asp Gly Ser Met Leu Lys Ala Val Ile
                115                 120                 125

Asp Gln Cys Asn His Asp Asn Ile Leu Arg Phe Gly Ile Ala Val Leu
    130                 135                 140

Gly Tyr Leu Asn Arg Asn Ala Leu Asp Thr Lys Asn Leu Ile Lys Glu
145                 150                 155                 160

Ile Lys Ala Ile Ala Ser Ile Pro Thr Glu Arg Tyr Phe Phe Asn Val
                165                 170                 175

Ser Asp Glu Ala Ala Leu Leu Glu Lys Ala Gly Thr Leu Gly Glu Gln
                180                 185                 190

Ile Phe Ser
        195

<210> SEQ ID NO 7
<211> LENGTH: 195
<212> TYPE: PRT
<213> ORGANISM: Homo sapiens

<400> SEQUENCE: 7

Cys Pro Thr Tyr Met Asp Val Val Ile Val Leu Asp Gly Ser Asn Ser
 1               5                  10                  15

Ile Tyr Pro Trp Ser Glu Val Gln Thr Phe Leu Arg Arg Leu Val Gly
                 20                  25                  30

Lys Leu Phe Ile Asp Pro Glu Gln Ile Gln Val Gly Leu Val Gln Tyr
         35                  40                  45

Gly Glu Ser Pro Val His Glu Trp Ser Leu Gly Asp Phe Arg Thr Lys
 50                  55                  60

Glu Glu Val Val Arg Ala Ala Lys Asn Leu Ser Arg Arg Glu Gly Arg
 65                  70                  75                  80

Glu Thr Lys Thr Ala Gln Ala Ile Met Val Ala Cys Thr Glu Gly Phe
                 85                  90                  95

Ser Gln Ser His Gly Gly Arg Pro Glu Ala Ala Arg Leu Leu Val Val
                100                 105                 110

Val Thr Asp Gly Glu Ser His Asp Gly Glu Glu Leu Pro Ala Ala Leu
                115                 120                 125

Lys Ala Cys Glu Ala Gly Arg Val Thr Arg Tyr Gly Ile Ala Val Leu
    130                 135                 140

Gly His Tyr Leu Arg Arg Gln Arg Asp Pro Ser Ser Phe Leu Arg Glu
145                 150                 155                 160

Ile Arg Thr Ile Ala Ser Asp Pro Asp Glu Arg Phe Phe Phe Asn Val
                165                 170                 175

Thr Asp Glu Ala Ala Leu Thr Asp Ile Val Asp Ala Leu Gly Asp Arg
                180                 185                 190

Ile Phe Gly
        195

<210> SEQ ID NO 8
<211> LENGTH: 193
<212> TYPE: PRT
<213> ORGANISM: Homo sapiens

<400> SEQUENCE: 8

Cys Gln Thr Tyr Met Asp Ile Val Ile Val Leu Asp Gly Ser Asn Ser
1               5                   10                  15

Ile Tyr Pro Trp Val Glu Val Gln His Phe Leu Ile Asn Ile Leu Lys
            20                  25                  30

Lys Phe Tyr Ile Gly Pro Gly Gln Ile Gln Val Gly Val Val Gln Tyr
        35                  40                  45

Gly Glu Asp Val Val His Glu Phe His Leu Asn Asp Tyr Arg Ser Val
    50                  55                  60

Lys Asp Val Val Glu Ala Ala Ser His Ile Glu Gln Arg Gly Gly Thr
65                  70                  75                  80

Glu Thr Arg Thr Ala Phe Gly Ile Glu Phe Ala Arg Ser Glu Ala Phe
                85                  90                  95

Gln Lys Gly Gly Arg Lys Gly Ala Lys Lys Val Met Ile Val Ile Thr
            100                 105                 110

Asp Gly Glu Ser His Asp Ser Pro Asp Leu Glu Lys Val Ile Gln Gln
        115                 120                 125

Ser Glu Arg Asp Asn Val Thr Arg Tyr Ala Val Ala Val Leu Gly Tyr
    130                 135                 140

Tyr Asn Arg Arg Gly Ile Asn Pro Glu Thr Phe Leu Asn Glu Ile Lys
145                 150                 155                 160

Tyr Ile Ala Ser Asp Pro Asp Lys His Phe Phe Asn Val Thr Asp
                165                 170                 175

Glu Ala Ala Leu Lys Asp Ile Val Asp Ala Leu Gly Asp Arg Ile Phe
                180                 185                 190

Ser

<210> SEQ ID NO 9
<211> LENGTH: 192
<212> TYPE: PRT
<213> ORGANISM: Homo sapiens

<400> SEQUENCE: 9

Glu Glu Ala Gly Thr Glu Ile Ala Ile Ile Leu Asp Gly Ser Gly Ser
1               5                   10                  15

Ile Asp Pro Pro Asp Phe Gln Arg Ala Lys Asp Phe Ile Ser Asn Met
            20                  25                  30

Met Arg Asn Phe Tyr Glu Lys Cys Phe Glu Cys Asn Phe Ala Leu Val
        35                  40                  45

Gln Tyr Gly Gly Val Ile Gln Thr Glu Phe Asp Leu Arg Asp Ser Gln
    50                  55                  60

Asp Val Met Ala Ser Leu Ala Arg Val Gln Asn Ile Thr Gln Val Gly
65                  70                  75                  80

Ser Val Thr Lys Thr Ala Ser Ala Met Gln His Val Leu Asp Ser Ile
                85                  90                  95

Phe Thr Ser Ser His Gly Ser Arg Arg Lys Ala Ser Lys Val Met Val
            100                 105                 110

Val Leu Thr Asp Gly Gly Ile Phe Glu Asp Pro Leu Asn Leu Thr Thr
        115                 120                 125

Val Ile Asn Ser Pro Lys Met Gln Gly Val Glu Arg Phe Ala Ile Gly

```
                130                 135                 140
Val Gly Glu Glu Phe Lys Ser Ala Arg Thr Ala Arg Glu Leu Asn Leu
145                 150                 155                 160

Ile Ala Ser Asp Pro Asp Glu Thr His Ala Phe Lys Val Thr Asn Tyr
                165                 170                 175

Met Ala Leu Asp Gly Leu Leu Ser Lys Leu Arg Tyr Asn Ile Ile Ser
                180                 185                 190

<210> SEQ ID NO 10
<211> LENGTH: 244
<212> TYPE: PRT
<213> ORGANISM: Homo sapiens

<400> SEQUENCE: 10

Tyr Pro Val Asp Ile Tyr Tyr Leu Met Asp Leu Ser Tyr Ser Met Lys
1               5                   10                  15

Asp Asp Leu Trp Ser Ile Gln Asn Leu Gly Thr Lys Leu Ala Thr Gln
                20                  25                  30

Met Arg Lys Leu Thr Ser Asn Leu Arg Ile Gly Phe Gly Ala Phe Val
            35                  40                  45

Asp Lys Pro Val Ser Pro Tyr Met Tyr Ile Ser Pro Pro Glu Ala Leu
        50                  55                  60

Glu Asn Pro Cys Tyr Asp Met Lys Thr Thr Cys Leu Pro Met Phe Gly
65                  70                  75                  80

Tyr Lys His Val Leu Thr Leu Thr Asp Gln Val Thr Arg Phe Asn Glu
                85                  90                  95

Glu Val Lys Lys Gln Ser Val Ser Arg Asn Arg Asp Ala Pro Glu Gly
                100                 105                 110

Gly Phe Asp Ala Ile Met Gln Ala Thr Val Cys Asp Glu Lys Ile Gly
            115                 120                 125

Trp Arg Asn Asp Ala Ser His Leu Leu Val Phe Thr Thr Asp Ala Lys
130                 135                 140

Thr His Ile Ala Leu Asp Gly Arg Leu Ala Gly Ile Val Gln Pro Asn
145                 150                 155                 160

Asp Gly Gln Cys His Val Gly Ser Asp Asn His Tyr Ser Ala Ser Thr
                165                 170                 175

Thr Met Asp Tyr Pro Ser Leu Gly Leu Met Thr Glu Lys Leu Ser Gln
                180                 185                 190

Lys Asn Ile Asn Leu Ile Phe Ala Val Thr Glu Asn Val Val Asn Leu
            195                 200                 205

Tyr Gln Asn Tyr Ser Glu Leu Ile Pro Gly Thr Thr Val Gly Val Leu
        210                 215                 220

Ser Met Asp Ser Ser Asn Val Leu Gln Leu Ile Val Asp Ala Tyr Gly
225                 230                 235                 240

Lys Ile Arg Ser

<210> SEQ ID NO 11
<211> LENGTH: 245
<212> TYPE: PRT
<213> ORGANISM: Homo sapiens

<400> SEQUENCE: 11

Tyr Pro Val Asp Leu Tyr Tyr Leu Met Asp Leu Ser Leu Ser Met Lys
1               5                   10                  15

Asp Asp Leu Asp Asn Ile Arg Ser Leu Gly Thr Lys Leu Ala Glu Glu
                20                  25                  30
```

```
Met Arg Lys Leu Thr Ser Asn Phe Arg Leu Gly Phe Gly Ser Phe Val
         35                  40                  45

Asp Lys Asp Ile Ser Pro Phe Ser Tyr Thr Ala Pro Arg Tyr Gln Thr
 50                  55                  60

Asn Pro Cys Ile Gly Tyr Lys Leu Phe Pro Asn Cys Val Pro Ser Phe
 65                  70                  75                  80

Gly Phe Arg His Leu Leu Pro Leu Thr Asp Arg Val Asp Ser Phe Asn
                 85                  90                  95

Glu Glu Val Arg Lys Gln Arg Val Ser Arg Asn Arg Asp Ala Pro Glu
                100                 105                 110

Gly Gly Phe Asp Ala Val Leu Gln Ala Ala Val Cys Lys Glu Lys Ile
                115                 120                 125

Gly Trp Arg Lys Asp Ala Leu His Leu Leu Val Phe Thr Thr Asp Asp
        130                 135                 140

Val Pro His Ile Ala Leu Asp Gly Lys Leu Gly Gly Leu Val Gln Pro
145                 150                 155                 160

His Asp Gly Gln Cys His Leu Asn Glu Ala Asn Glu Tyr Thr Ala Ser
                165                 170                 175

Asn Gln Met Asp Tyr Pro Ser Leu Ala Leu Leu Gly Glu Lys Leu Ala
                180                 185                 190

Glu Asn Asn Ile Asn Leu Ile Phe Ala Val Thr Lys Asn His Tyr Met
                195                 200                 205

Leu Tyr Lys Asn Phe Thr Ala Leu Ile Pro Gly Thr Thr Val Glu Ile
        210                 215                 220

Leu Asp Gly Asp Ser Lys Asn Ile Ile Gln Leu Ile Ile Asn Ala Tyr
225                 230                 235                 240

Asn Ser Ile Arg Ser
                245

<210> SEQ ID NO 12
<211> LENGTH: 243
<212> TYPE: PRT
<213> ORGANISM: Homo sapiens

<400> SEQUENCE: 12

Tyr Pro Val Asp Leu Tyr Tyr Leu Met Asp Leu Ser Ala Ser Met Asp
 1               5                  10                  15

Asp Asp Leu Asn Thr Ile Lys Glu Leu Gly Ser Arg Leu Ser Lys Glu
                20                  25                  30

Met Ser Lys Leu Thr Ser Asn Phe Arg Leu Gly Phe Gly Ser Phe Val
         35                  40                  45

Glu Lys Pro Val Ser Pro Phe Val Lys Thr Thr Pro Glu Glu Ile Ala
 50                  55                  60

Asn Pro Cys Ser Ser Ile Pro Tyr Phe Cys Leu Pro Thr Phe Gly Phe
 65                  70                  75                  80

Lys His Ile Leu Pro Leu Thr Asn Asp Ala Glu Arg Phe Asn Glu Ile
                 85                  90                  95

Val Lys Asn Gln Lys Ile Ser Ala Asn Ile Asp Thr Pro Glu Gly Gly
                100                 105                 110

Phe Asp Ala Ile Met Gln Ala Ala Val Cys Lys Glu Lys Ile Gly Trp
        115                 120                 125

Arg Asn Asp Ser Leu His Leu Leu Val Phe Val Ser Asp Ala Asp Ser
        130                 135                 140

His Phe Gly Met Asp Ser Lys Leu Ala Gly Ile Val Ile Pro Asn Asp
145                 150                 155                 160
```

-continued

```
Gly Leu Cys His Leu Asp Ser Lys Asn Glu Tyr Ser Met Ser Thr Val
            165                 170                 175

Leu Glu Tyr Pro Thr Ile Gly Gln Leu Ile Asp Lys Leu Val Gln Asn
        180                 185                 190

Asn Val Leu Leu Ile Phe Ala Val Thr Gln Glu Gln Val His Leu Tyr
        195                 200                 205

Glu Asn Tyr Ala Lys Leu Ile Pro Gly Ala Thr Val Gly Leu Leu Gln
        210                 215                 220

Lys Asp Ser Gly Asn Ile Leu Gln Leu Ile Ile Ser Ala Tyr Glu Glu
225                 230                 235                 240

Leu Arg Ser
```

<210> SEQ ID NO 13
<211> LENGTH: 240
<212> TYPE: PRT
<213> ORGANISM: Homo sapiens

<400> SEQUENCE: 13

```
Tyr Pro Ile Asp Leu Tyr Tyr Leu Met Asp Leu Ser Tyr Ser Met Lys
1               5                   10                  15

Asp Asp Leu Glu Asn Val Lys Ser Leu Gly Thr Asp Leu Met Asn Glu
            20                  25                  30

Met Arg Arg Ile Thr Ser Asp Phe Arg Ile Gly Phe Gly Ser Phe Val
        35                  40                  45

Glu Lys Thr Val Met Pro Tyr Ile Ser Thr Thr Pro Ala Lys Leu Arg
    50                  55                  60

Asn Pro Cys Thr Ser Glu Gln Asn Cys Thr Thr Pro Phe Ser Tyr Lys
65                  70                  75                  80

Asn Val Leu Ser Leu Thr Asn Lys Gly Glu Val Phe Asn Glu Leu Val
                85                  90                  95

Gly Lys Gln Arg Ile Ser Gly Asn Leu Asp Ser Pro Glu Gly Gly Phe
            100                 105                 110

Asp Ala Ile Met Gln Val Ala Val Cys Gly Ser Leu Ile Gly Trp Arg
        115                 120                 125

Asn Val Thr Arg Leu Leu Val Phe Ser Thr Asp Ala Gly Phe His Phe
    130                 135                 140

Ala Gly Asp Gly Lys Leu Gly Gly Ile Val Leu Pro Asn Asp Gly Gln
145                 150                 155                 160

Cys His Leu Glu Asn Asn Met Tyr Thr Met Ser His Tyr Tyr Asp Tyr
                165                 170                 175

Pro Ser Ile Ala His Leu Val Gln Lys Leu Ser Glu Asn Asn Ile Gln
            180                 185                 190

Thr Ile Phe Ala Val Thr Glu Glu Phe Gln Pro Val Tyr Lys Glu Leu
        195                 200                 205

Lys Asn Leu Ile Pro Lys Ser Ala Val Gly Thr Leu Ser Ala Asn Ser
    210                 215                 220

Ser Asn Val Ile Gln Leu Ile Ile Asp Ala Tyr Asn Ser Leu Ser Ser
225                 230                 235                 240
```

<210> SEQ ID NO 14
<211> LENGTH: 241
<212> TYPE: PRT
<213> ORGANISM: Homo sapiens

<400> SEQUENCE: 14

```
Tyr Pro Ile Asp Leu Tyr Tyr Leu Met Asp Leu Ser Tyr Ser Met Leu
1               5                   10                  15
```

Asp Asp Leu Arg Asn Val Lys Lys Leu Gly Asp Leu Leu Arg Ala
        20                  25                  30

Leu Asn Glu Ile Thr Glu Ser Gly Arg Ile Gly Phe Gly Ser Phe Val
        35                  40                  45

Asp Lys Thr Val Leu Pro Phe Val Asn Thr His Pro Asp Lys Leu Arg
50                  55                  60

Asn Pro Cys Pro Asn Lys Glu Lys Glu Cys Gln Pro Pro Phe Ala Phe
65                  70                  75                  80

Arg His Val Leu Lys Leu Thr Asn Asn Ser Asn Gln Phe Gln Thr Glu
                85                  90                  95

Val Gly Lys Gln Leu Ile Ser Gly Asn Leu Asp Ala Pro Glu Gly Gly
                100                 105                 110

Leu Asp Ala Met Met Gln Val Ala Ala Cys Pro Glu Glu Ile Gly Trp
        115                 120                 125

Arg Asn Val Thr Arg Leu Leu Val Phe Ala Thr Asp Asp Gly Phe His
130                 135                 140

Phe Ala Gly Asp Gly Lys Leu Gly Ala Ile Leu Thr Pro Asn Asp Gly
145                 150                 155                 160

Arg Cys His Leu Glu Asp Asn Leu Tyr Lys Arg Ser Asn Glu Phe Asp
                165                 170                 175

Tyr Pro Ser Val Gly Gln Leu Ala His Lys Leu Ala Glu Asn Asn Ile
        180                 185                 190

Gln Pro Ile Phe Ala Val Thr Ser Arg Met Val Lys Thr Tyr Glu Lys
        195                 200                 205

Leu Thr Glu Ile Ile Pro Lys Ser Ala Val Gly Glu Leu Ser Glu Asp
        210                 215                 220

Ser Ser Asn Val Val Gln Leu Ile Lys Asn Ala Tyr Asn Lys Leu Ser
225                 230                 235                 240

Ser

<210> SEQ ID NO 15
<211> LENGTH: 242
<212> TYPE: PRT
<213> ORGANISM: Homo sapiens

<400> SEQUENCE: 15

Tyr Pro Val Asp Leu Tyr Tyr Leu Met Asp Leu Ser Tyr Ser Met Lys
1               5                   10                  15

Asp Asp Leu Glu Arg Val Arg Gln Leu Gly His Ala Leu Leu Val Arg
        20                  25                  30

Leu Gln Glu Val Thr His Ser Val Arg Ile Gly Phe Gly Ser Phe Val
        35                  40                  45

Asp Lys Thr Val Leu Pro Phe Val Ser Thr Val Pro Ser Lys Leu Arg
50                  55                  60

His Pro Cys Pro Thr Arg Leu Glu Arg Cys Gln Ser Pro Phe Ser Phe
65                  70                  75                  80

His His Val Leu Ser Leu Thr Gly Asp Ala Gln Ala Phe Glu Arg Glu
                85                  90                  95

Val Gly Arg Gln Ser Val Ser Gly Asn Leu Asp Ser Pro Glu Gly Gly
                100                 105                 110

Phe Asp Ala Ile Leu Gln Ala Ala Leu Cys Gln Glu Gln Ile Gly Trp
        115                 120                 125

Arg Asn Val Ser Arg Leu Leu Val Phe Thr Ser Asp Asp Thr Phe His
130                 135                 140

```
Thr Ala Gly Asp Gly Lys Leu Gly Gly Ile Phe Met Pro Ser Asp Gly
145                 150                 155                 160

His Cys His Leu Asp Ser Asn Gly Leu Tyr Ser Arg Ser Thr Glu Phe
                165                 170                 175

Asp Tyr Pro Ser Val Gly Gln Val Ala Gln Ala Leu Ser Ala Ala Asn
            180                 185                 190

Ile Gln Pro Ile Phe Ala Val Thr Ser Ala Ala Leu Pro Val Tyr Gln
        195                 200                 205

Glu Leu Ser Lys Leu Ile Pro Lys Ser Ala Val Gly Glu Leu Ser Glu
    210                 215                 220

Asp Ser Ser Asn Val Val Gln Leu Ile Met Asp Ala Tyr Asn Ser Leu
225                 230                 235                 240

Ser Ser

<210> SEQ ID NO 16
<211> LENGTH: 242
<212> TYPE: PRT
<213> ORGANISM: Homo sapiens

<400> SEQUENCE: 16

Tyr Pro Val Asp Leu Tyr Tyr Leu Val Asp Val Ser Ala Ser Met His
1               5                   10                  15

Asn Asn Ile Glu Lys Leu Asn Ser Val Gly Asn Asp Leu Ser Arg Lys
            20                  25                  30

Met Ala Phe Phe Ser Arg Asp Phe Arg Leu Gly Phe Gly Ser Tyr Val
        35                  40                  45

Asp Lys Thr Val Ser Pro Tyr Ile Ser Ile His Pro Glu Arg Ile His
50                  55                  60

Asn Gln Cys Ser Asp Tyr Asn Leu Asp Cys Met Pro Pro His Gly Tyr
65                  70                  75                  80

Ile His Val Leu Ser Leu Thr Glu Asn Ile Thr Glu Phe Glu Lys Ala
                85                  90                  95

Val His Arg Gln Lys Ile Ser Gly Asn Ile Asp Thr Pro Glu Gly Gly
            100                 105                 110

Phe Asp Ala Met Leu Gln Ala Ala Val Cys Glu Ser His Ile Gly Trp
        115                 120                 125

Arg Lys Glu Ala Lys Arg Leu Leu Leu Val Met Thr Asp Gln Thr Ser
130                 135                 140

His Leu Ala Leu Asp Ser Lys Leu Ala Gly Ile Val Val Pro Asn Asp
145                 150                 155                 160

Gly Asn Cys His Leu Lys Asn Asn Val Tyr Val Lys Ser Thr Thr Met
                165                 170                 175

Glu His Pro Ser Leu Gly Gln Leu Ser Glu Lys Leu Ile Asp Asn Asn
            180                 185                 190

Ile Asn Val Ile Phe Ala Val Gln Gly Lys Gln Phe His Trp Tyr Lys
        195                 200                 205

Asp Leu Leu Pro Leu Leu Pro Gly Thr Ile Ala Gly Glu Ile Glu Ser
210                 215                 220

Lys Ala Ala Asn Leu Asn Asn Leu Val Val Glu Ala Tyr Gln Lys Leu
225                 230                 235                 240

Ile Ser

<210> SEQ ID NO 17
<211> LENGTH: 241
<212> TYPE: PRT
<213> ORGANISM: Homo sapiens
```

<400> SEQUENCE: 17

| Ser | Pro | Val | Asp | Leu | Tyr | Ile | Leu | Met | Asp | Phe | Ser | Asn | Ser | Met | Ser |
| 1 | | | | 5 | | | | | 10 | | | | | 15 | |

| Asp | Asp | Leu | Asp | Asn | Leu | Lys | Lys | Met | Gly | Gln | Asn | Leu | Ala | Arg | Val |
| | | | 20 | | | | | 25 | | | | | 30 | | |

| Leu | Ser | Gln | Leu | Thr | Ser | Asp | Tyr | Thr | Ile | Gly | Phe | Gly | Lys | Phe | Val |
| | | | 35 | | | | | 40 | | | | | 45 | | |

| Asp | Lys | Val | Ser | Val | Pro | Gln | Thr | Asp | Met | Arg | Pro | Glu | Lys | Leu | Lys |
| | 50 | | | | | 55 | | | | | 60 | | | | |

| Glu | Pro | Trp | Pro | Asn | Ser | Asp | Pro | Pro | Phe | Ser | Phe | Lys | Asn | Val | Ile |
| 65 | | | | | 70 | | | | | 75 | | | | | 80 |

| Ser | Leu | Thr | Glu | Asp | Val | Asp | Glu | Phe | Arg | Asn | Lys | Leu | Gln | Gly | Glu |
| | | | | 85 | | | | | 90 | | | | | 95 | |

| Arg | Ile | Ser | Gly | Asn | Leu | Asp | Ala | Pro | Glu | Gly | Gly | Phe | Asp | Ala | Ile |
| | | | 100 | | | | | 105 | | | | | 110 | | |

| Leu | Gln | Thr | Ala | Val | Cys | Thr | Arg | Asp | Ile | Gly | Trp | Arg | Pro | Asp | Ser |
| | | | 115 | | | | | 120 | | | | | 125 | | |

| Thr | His | Leu | Leu | Val | Phe | Ser | Thr | Glu | Ser | Ala | Phe | His | Tyr | Glu | Ala |
| | | | 130 | | | | | 135 | | | | | 140 | | |

| Asp | Gly | Ala | Asn | Val | Leu | Ala | Gly | Ile | Met | Ser | Arg | Asn | Asp | Glu | Arg |
| 145 | | | | | 150 | | | | | 155 | | | | | 160 |

| Cys | His | Leu | Asp | Thr | Thr | Gly | Thr | Tyr | Thr | Gln | Tyr | Arg | Thr | Gln | Asp |
| | | | | 165 | | | | | 170 | | | | | 175 | |

| Tyr | Pro | Ser | Val | Pro | Thr | Leu | Val | Arg | Leu | Leu | Ala | Lys | His | Asn | Ile |
| | | | 180 | | | | | 185 | | | | | 190 | | |

| Ile | Pro | Ile | Phe | Ala | Val | Thr | Asn | Tyr | Ser | Tyr | Ser | Tyr | Tyr | Glu | Lys |
| | | | 195 | | | | | 200 | | | | | 205 | | |

| Leu | His | Thr | Tyr | Phe | Pro | Val | Ser | Ser | Leu | Gly | Val | Leu | Gln | Glu | Asp |
| | | | 210 | | | | | 215 | | | | | 220 | | |

| Ser | Ser | Asn | Ile | Val | Glu | Leu | Leu | Glu | Glu | Ala | Phe | Asn | Arg | Ile | Arg |
| 225 | | | | | 230 | | | | | 235 | | | | | 240 |

Ser

<210> SEQ ID NO 18
<211> LENGTH: 42
<212> TYPE: DNA
<213> ORGANISM: Artificial Sequence
<220> FEATURE:
<223> OTHER INFORMATION: mutagenic primer

<400> SEQUENCE: 18
tataggatcc gaggccctcc gagggagtcc tcaagaggat ag         42

<210> SEQ ID NO 19
<211> LENGTH: 40
<212> TYPE: DNA
<213> ORGANISM: Artificial Sequence
<220> FEATURE:
<223> OTHER INFORMATION: mutagenic primer

<400> SEQUENCE: 19
ctactcgagt tacttctccc gaagctggtt ctgaatggtc           40

<210> SEQ ID NO 20
<211> LENGTH: 36
<212> TYPE: DNA
<213> ORGANISM: Artificial Sequence
<220> FEATURE:

<223> OTHER INFORMATION: mutagenic primer

<400> SEQUENCE: 20
ctactcgagt taaccctcga tcgcaaagcc cttctc            36

<210> SEQ ID NO 21
<211> LENGTH: 43
<212> TYPE: PRT
<213> ORGANISM: Homo sapiens

<400> SEQUENCE: 21

```
Phe Glu Ala Leu Lys Thr Ile Gln Asn Gln Leu Arg Glu Lys Ile Phe
  1               5                  10                  15

Ala Ile Glu Gly Thr Gln Thr Gly Ser Ser Ser Ser Phe Glu His Glu
             20                  25                  30

Met Ser Gln Glu Gly Phe Ser Ala Ala Ile Thr
         35                  40
```

<210> SEQ ID NO 22
<211> LENGTH: 43
<212> TYPE: PRT
<213> ORGANISM: Homo sapiens

<400> SEQUENCE: 22

```
Phe Asp Ala Leu Lys Asp Ile Gln Asn Gln Leu Lys Glu Lys Ile Phe
  1               5                  10                  15

Ala Ile Glu Gly Thr Glu Thr Thr Ser Ser Ser Ser Phe Glu Leu Glu
             20                  25                  30

Met Ala Gln Glu Gly Phe Ser Ala Val Phe Thr
         35                  40
```

<210> SEQ ID NO 23
<211> LENGTH: 43
<212> TYPE: PRT
<213> ORGANISM: Homo sapiens

<400> SEQUENCE: 23

```
Phe Ala Ala Leu Gly Ser Ile Gln Lys Gln Leu Gln Leu Lys Ile Tyr
  1               5                  10                  15

Ala Val Glu Gly Thr Gln Ser Arg Ala Ser Ser Ser Phe Gln His Glu
             20                  25                  30

Met Ser Gln Glu Gly Phe Ser Thr Ala Leu Thr
         35                  40
```

<210> SEQ ID NO 24
<211> LENGTH: 43
<212> TYPE: PRT
<213> ORGANISM: Homo sapiens

<400> SEQUENCE: 24

```
Phe Glu Lys Leu Lys Asp Leu Phe Thr Glu Leu Gln Lys Lys Ile Tyr
  1               5                  10                  15

Val Ile Glu Gly Thr Ser Lys Gln Asp Leu Thr Ser Phe Asn Met Glu
             20                  25                  30

Leu Ser Ser Ser Gly Ile Ser Ala Asp Leu Ser
         35                  40
```

<210> SEQ ID NO 25
<211> LENGTH: 42
<212> TYPE: PRT
<213> ORGANISM: Homo sapiens

```
<400> SEQUENCE: 25

Glu Ala Ala Leu Lys Asp Ile Val Asp Ala Leu Gly Asp Arg Ile Phe
1               5                   10                  15

Ser Leu Glu Gly Thr Asn Lys Asn Gly Thr Ser Phe Gly Leu Glu Met
            20                  25                  30

Ser Gln Thr Gly Phe Ser Ser His Val Val
        35                  40

<210> SEQ ID NO 26
<211> LENGTH: 43
<212> TYPE: PRT
<213> ORGANISM: Homo sapiens

<400> SEQUENCE: 26

Glu Ala Ala Leu Thr Asp Ile Val Asp Ala Leu Gly Asp Arg Ile Phe
1               5                   10                  15

Gly Leu Glu Gly Ser His Ala Glu Asn Glu Ser Ser Phe Gly Leu Glu
            20                  25                  30

Met Ser Gln Ile Gly Phe Ser Thr His Arg Leu
        35                  40

<210> SEQ ID NO 27
<211> LENGTH: 43
<212> TYPE: PRT
<213> ORGANISM: Homo sapiens

<400> SEQUENCE: 27

Glu Leu Ala Leu Val Thr Ile Val Lys Thr Leu Gly Glu Arg Ile Phe
1               5                   10                  15

Ala Leu Glu Ala Thr Ala Asp Gln Ser Ala Ala Ser Phe Glu Met Glu
            20                  25                  30

Met Ser Gln Thr Gly Phe Ser Ala His Tyr Ser
        35                  40

<210> SEQ ID NO 28
<211> LENGTH: 42
<212> TYPE: PRT
<213> ORGANISM: Homo sapiens

<400> SEQUENCE: 28

Glu Ala Ala Leu Leu Glu Lys Ala Gly Thr Leu Gly Glu Gln Ile Phe
1               5                   10                  15

Ser Ile Glu Gly Thr Val Gln Gly Gly Asp Asn Phe Gln Met Glu Met
            20                  25                  30

Ser Gln Val Gly Phe Ser Ala Asp Tyr Ser
        35                  40

<210> SEQ ID NO 29
<211> LENGTH: 40
<212> TYPE: PRT
<213> ORGANISM: Homo sapiens

<400> SEQUENCE: 29

Tyr Met Ala Leu Asp Gly Leu Leu Ser Lys Leu Arg Tyr Asn Ile Ile
1               5                   10                  15

Ser Met Glu Gly Thr Val Gly Asp Ala Leu His Tyr Gln Leu Ala Gln
            20                  25                  30

Ile Gly Phe Ser Ala Gln Ile Leu
        35                  40
```

<210> SEQ ID NO 30
<211> LENGTH: 1153
<212> TYPE: PRT
<213> ORGANISM: Homo sapiens

<400> SEQUENCE: 30

```
Met Ala Leu Arg Val Leu Leu Thr Ala Leu Thr Leu Cys His Gly
 1               5                  10                  15

Phe Asn Leu Asp Thr Glu Asn Ala Met Thr Phe Gln Glu Asn Ala Arg
                20                  25                  30

Gly Phe Gly Gln Ser Val Val Gln Leu Gln Gly Ser Arg Val Val Val
            35                  40                  45

Gly Ala Pro Gln Glu Ile Val Ala Ala Asn Gln Arg Gly Ser Leu Tyr
        50                  55                  60

Gln Cys Asp Tyr Ser Thr Gly Ser Cys Glu Pro Ile Arg Leu Gln Val
 65                  70                  75                  80

Pro Val Glu Ala Val Asn Met Ser Leu Gly Leu Ser Leu Ala Ala Thr
                85                  90                  95

Thr Ser Pro Pro Gln Leu Leu Ala Cys Gly Pro Thr Val His Gln Thr
                100                 105                 110

Cys Ser Glu Asn Thr Tyr Val Lys Gly Leu Cys Phe Leu Phe Gly Ser
            115                 120                 125

Asn Leu Arg Gln Gln Pro Gln Lys Phe Pro Glu Ala Leu Arg Gly Cys
    130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
                180                 185                 190

Ser Glu Glu Phe Arg Ile His Phe Thr Phe Lys Glu Phe Gln Asn Asn
            195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
                260                 265                 270

Pro Glu Ala Asp Arg Glu Gly Val Ile Arg Tyr Val Ile Gly Val Gly
            275                 280                 285

Asp Ala Phe Arg Ser Glu Lys Ser Arg Gln Glu Leu Asn Thr Ile Ala
    290                 295                 300

Ser Lys Pro Pro Arg Asp His Val Phe Gln Val Asn Asn Phe Glu Ala
305                 310                 315                 320

Leu Lys Thr Ile Gln Asn Gln Leu Arg Glu Lys Ile Phe Ala Ile Glu
                325                 330                 335

Gly Thr Gln Thr Gly Ser Ser Ser Ser Phe Glu His Glu Met Ser Gln
                340                 345                 350

Glu Gly Phe Ser Ala Ala Ile Thr Ser Asn Gly Pro Leu Leu Ser Thr
            355                 360                 365

Val Gly Ser Tyr Asp Trp Ala Gly Gly Val Phe Leu Tyr Thr Ser Lys
    370                 375                 380

Glu Lys Ser Thr Phe Ile Asn Met Thr Arg Val Asp Ser Asp Met Asn
```

```
                385                 390                 395                 400
Asp Ala Tyr Leu Gly Tyr Ala Ala Ile Ile Leu Arg Asn Arg Val
            405                 410                 415
Gln Ser Leu Val Leu Gly Ala Pro Arg Tyr Gln His Ile Gly Leu Val
            420                 425                 430
Ala Met Phe Arg Gln Asn Thr Gly Met Trp Glu Ser Asn Ala Asn Val
            435                 440                 445
Lys Gly Thr Gln Ile Gly Ala Tyr Phe Gly Ala Ser Leu Cys Ser Val
            450                 455                 460
Asp Val Asp Ser Asn Gly Ser Thr Asp Leu Val Leu Ile Gly Ala Pro
465                 470                 475                 480
His Tyr Tyr Glu Gln Thr Arg Gly Gly Gln Val Ser Val Cys Pro Leu
            485                 490                 495
Pro Arg Gly Gln Arg Ala Arg Trp Gln Cys Asp Ala Val Leu Tyr Gly
            500                 505                 510
Glu Gln Gly Gln Pro Trp Gly Arg Phe Gly Ala Ala Leu Thr Val Leu
            515                 520                 525
Gly Asp Val Asn Gly Asp Lys Leu Thr Asp Val Ala Ile Gly Ala Pro
530                 535                 540
Gly Glu Glu Asp Asn Arg Gly Ala Val Tyr Leu Phe His Gly Thr Ser
545                 550                 555                 560
Gly Ser Gly Ile Ser Pro Ser His Ser Gln Arg Ile Ala Gly Ser Lys
            565                 570                 575
Leu Ser Pro Arg Leu Gln Tyr Phe Gly Gln Ser Leu Ser Gly Gly Gln
            580                 585                 590
Asp Leu Thr Met Asp Gly Leu Val Asp Leu Thr Val Gly Ala Gln Gly
            595                 600                 605
His Val Leu Leu Leu Arg Ser Gln Pro Val Leu Arg Val Lys Ala Ile
            610                 615                 620
Met Glu Phe Asn Pro Arg Glu Val Ala Arg Asn Val Phe Glu Cys Asn
625                 630                 635                 640
Asp Gln Val Val Lys Gly Lys Glu Ala Gly Glu Val Arg Val Cys Leu
            645                 650                 655
His Val Gln Lys Ser Thr Arg Asp Arg Leu Arg Glu Gly Gln Ile Gln
            660                 665                 670
Ser Val Val Thr Tyr Asp Leu Ala Leu Asp Ser Gly Arg Pro His Ser
            675                 680                 685
Arg Ala Val Phe Asn Glu Thr Lys Asn Ser Thr Arg Arg Gln Thr Gln
            690                 695                 700
Val Leu Gly Leu Thr Gln Thr Cys Glu Thr Leu Lys Leu Gln Leu Pro
705                 710                 715                 720
Asn Cys Ile Glu Asp Pro Val Ser Pro Ile Val Leu Arg Leu Asn Phe
            725                 730                 735
Ser Leu Val Gly Thr Pro Leu Ser Ala Phe Gly Asn Leu Arg Pro Val
            740                 745                 750
Leu Ala Glu Asp Ala Gln Arg Leu Phe Thr Ala Leu Phe Pro Phe Glu
            755                 760                 765
Lys Asn Cys Gly Asn Asp Asn Ile Cys Gln Asp Asp Leu Ser Ile Thr
            770                 775                 780
Phe Ser Phe Met Ser Leu Asp Cys Leu Val Val Gly Gly Pro Arg Glu
785                 790                 795                 800
Phe Asn Val Thr Val Thr Val Arg Asn Asp Gly Glu Asp Ser Tyr Arg
            805                 810                 815
```

```
Thr Gln Val Thr Phe Phe Pro Leu Asp Leu Ser Tyr Arg Lys Val
            820             825             830

Ser Thr Leu Gln Asn Gln Arg Ser Gln Arg Ser Trp Arg Leu Ala Cys
        835             840             845

Glu Ser Ala Ser Ser Thr Glu Val Ser Gly Ala Leu Lys Ser Thr Ser
850             855             860

Cys Ser Ile Asn His Pro Ile Phe Pro Glu Asn Ser Glu Val Thr Phe
865             870             875             880

Asn Ile Thr Phe Asp Val Asp Ser Lys Ala Ser Leu Gly Asn Lys Leu
                885             890             895

Leu Leu Lys Ala Asn Val Thr Ser Glu Asn Asn Met Pro Arg Thr Asn
            900             905             910

Lys Thr Glu Phe Gln Leu Glu Leu Pro Val Lys Tyr Ala Val Tyr Met
        915             920             925

Val Val Thr Ser His Gly Val Ser Thr Lys Tyr Leu Asn Phe Thr Ala
    930             935             940

Ser Glu Asn Thr Ser Arg Val Met Gln His Gln Tyr Gln Val Ser Asn
945             950             955             960

Leu Gly Gln Arg Ser Leu Pro Ile Ser Leu Val Phe Leu Val Pro Val
                965             970             975

Arg Leu Asn Gln Thr Val Ile Trp Asp Arg Pro Gln Val Thr Phe Ser
            980             985             990

Glu Asn Leu Ser Ser Thr Cys His Thr Lys Glu Arg Leu Pro Ser His
        995             1000            1005

Ser Asp Phe Leu Ala Glu Leu Arg Lys Ala Pro Val Val Asn Cys Ser
    1010            1015            1020

Ile Ala Val Cys Gln Arg Ile Gln Cys Asp Ile Pro Phe Phe Gly Ile
1025            1030            1035            1040

Gln Glu Glu Phe Asn Ala Thr Leu Lys Gly Asn Leu Ser Phe Asp Trp
                1045            1050            1055

Tyr Ile Lys Thr Ser His Asn His Leu Leu Ile Val Ser Thr Ala Glu
            1060            1065            1070

Ile Leu Phe Asn Asp Ser Val Phe Thr Leu Leu Pro Gly Gln Gly Ala
        1075            1080            1085

Phe Val Arg Ser Gln Thr Glu Thr Lys Val Glu Pro Phe Glu Val Pro
    1090            1095            1100

Asn Pro Leu Pro Leu Ile Val Gly Ser Ser Val Gly Gly Leu Leu Leu
1105            1110            1115            1120

Leu Ala Leu Ile Thr Ala Ala Leu Tyr Lys Leu Gly Phe Phe Lys Arg
                1125            1130            1135

Gln Tyr Lys Asp Met Met Ser Glu Gly Gly Pro Pro Gly Ala Glu Pro
            1140            1145            1150

Gln
```

INTEGRIN-BINDING ANTIBODIES

RELATED APPLICATION INFORMATION

This application is a continuation of U.S. patent application Ser. No. 10/144,259, filed on May 10, 2002, now U.S. Pat. No. 7,323,552, the contents of which are hereby incorporated by reference.

STATEMENT AS TO FEDERALLY SPONSORED RESEARCH

This invention was made with government support under Grant Nos. DK48549 and HL54227 awarded by the National Institutes of Health. The U.S. Government has certain rights in this invention.

BACKGROUND

Integrins are heterodimeric receptors that mediate a wide variety of important interactions both between cells and between cells and the extracellular matrix via ligand binding. All integrins have an α subunit and a β subunit. Within the α subunit a region referred to as the A domain (or I domain) is known to be an important mediator of ligand binding. A similar region, the A-like domain, is present in many β subunits. These heterodimeric αβ integrins contain a von Willebrand Factor (vWF) A domain, βA, in their β subunits; and nine integrins also contain a second such domain, αA, in their α subunits. Many integrins are thought to exist in two conformations, a low affinity state (the "closed" or "unliganded" conformation) and a high affinity state (the "open" or "liganded" conformation), the latter of which is responsible for high affinity ligand binding.

Integrins transduce signals that mediate the effects of the matrix on the physiological activity of cells (e.g., motility, proliferation, differentiation). Moreover, integrins play a role in inflammation and in oncogenic cell transformation, metastasis, and apoptosis. Thus, there is considerable interest in identifying compounds that can activate or inhibit the activity of one or more integrins.

In order for an efficient integrin-ligand binding to occur, it is thought that the integrin must be in its high affinity configuration. It appears that inside-out signals generated when cells are activated by a variety of stimuli apparently switch integrins from a low affinity state to a high affinity state. This functional upregulation is associated with conformational changes in the extracellular regions of integrins that include the A domain of the α subunit and the A-like domain of the β subunit (Smith et al. 1988 *J. Biol. Chem.* 263:18726).

The integrin A-domain assumes a dinucleotide-binding fold (Lee et al. 1995 *Cell* 80:631; Emsley et al. 1997 *J. Biol. Chem.* 272:28512; Li et al. 1998 *J. Cell Biol.* 143:1523; Nolte et al. 1999 *FEBS Lett.* 452:379; and Legge et al. 2000 *J. Mol. Biol.* 295:1251), with a metal ion dependent adhesion site (MIDAS) on its top, and is connected through a C-terminal α7 helix at its bottom to the body of the integrin. MIDAS and its surrounding exposed side-chains form the binding site for physiologic ligands (Li et al., supra; Michishita et al. 1993 *Cell* 72:857-867; Kamata et al. 1994 *J. Biol. Chem.* 269: 26006-26010; Kern et al. 1994 *J. Biol. Chem.* 269:22811-6; Edwards et al. 1998 *J. Biol. Chem.* 273:28937-44; Zhang et al. 1999 *Biochemistry* 38:8064-71) and certain antagonists (Rieu et al. 1996 *J. Biol. Chem.* 271:15858-15861). In the "open" conformation, three non-charged resides in the protein directly coordinate the metal ion in MIDAS, a pseudoligand or ligand glutamate residue (Lee et al., supra; Li et al., supra; Emsley et al. 2000 *Cell* 100:47-56) completes metal coordination. In the "closed" form, the amphipathic C-terminal α7 helix is shifted upwards by 10 Å compared to the "open" form, wrapping around the rest of the domain. This large shift is associated with a change in metal coordination, where one of the three coordinating residues, a threonine, is now replaced with an aspartate, and a water molecule replaces the glutamate in completing the metal ion coordination sphere (Lee et al. 1995 *Structure* 3:1333-1340). These changes in metal coordination and topology of MIDAS are similar to those described in the structurally homologous G proteins (Lee et al., supra).

The crystal structure of four integrin A-domains (CD11b, CD11a, CD49a and CD49b) have been reported to date (Lee et al., supra; Lee et al. 1995 *Structure* 3:1333; Emsley et al., supra; Li et al., supra; Emsley et al. 1997 *J. Biol. Chem.* 272:28512). All, with the exception of integrin CD11b A-domain (11bA), were found only in the "closed" form, leading to the suggestion that the "open" form is a non-informative crystal artifact (Baldwin et al. 1998 *Structure* 6:923-935). Three studies support the view that the "open" form of the integrin A-domain equates with the "high" affinity state (Li et al. 1998 *J. Cell Biol.* 143:1523; Rieu et al., supra; Oxvig et al. 1999 *Proc. Nat'l Acad. Sci. USA* 96:2215-20). In the first, point mutations in CD11bA that are predicted on structural grounds to destabilize the "closed" structure, increased the proportion of the "high affinity" form in solution (Li et al. 1998 *J. Cell Biol.* 143:1523). In the second, the binding site for an "activation-dependent" monoclonal antibody mapped to a conformationally sensitive region of the A-domain (Oxvig et al., supra). The third study showed that an A-domain in complex with a short collagen peptide assumed the "open" conformation, and suggested that the "open" form can only be obtained in the presence of ligand (Emsley et al., supra). While it has been suggested that the ligand causes the conformational change in integrins, at least one study suggests that integrins can exist in high affinity state even in the absence of ligand (Smith and Cheresh 1988 *J. Biol. Chem.* 263:18726-31). In addition, several studies suggested that ligand binding affinity in heterodimeric integrins can be altered in an allosteric manner (Li et al. 1998 *J. Cell Biol.* 143:1523; Edwards et al. 1998 *J. Biol. Chem.* 273:28937-28944; Calderwood et al. 1998 *J. Biol. Chem.* 273:5625; Zhang et al. 1996 *J. Biol. Chem.* 271: 29953-7).

SUMMARY

The invention features polypeptides comprising all or part of a variant integrin α subunit A domain or a variant integrin β subunit A-like domain. In the polypeptides of the invention, referred to as variant integrin polypeptides, an important isoleucine or glutamic acid residue (described in greater detail below) is deleted or substituted.

The important isoleucine residue can be either deleted or replaced with different amino acids residue, preferably a smaller or less hydrophobic amino acid residue, e.g., alanine or glycine. Because the variant integrin polypeptides of the invention lacking the important isoleucine residue tend to exist in solution in a high affinity conformation, they are useful in screening assays for the identification of molecules that bind to (and/or modulate the activity of) an integrin. They are also useful for generating antibodies, e.g., monoclonal antibodies, which bind to the high affinity form of an integrin. Some such antibodies recognize an epitope that is either not present or not accessible on an integrin that is in a lower affinity conformation. Thus, the invention features antibodies which bind with greater affinity to a variant integrin of the invention than to corresponding wild-type integrin. The variant integrins lacking the important isoleucine can also be used to identify activation-specific ligands and be more sensitive than wild-type integrins for the identification of ligands in screening assays.

The important glutamic acid residue can be replaced by any other amino acid, e.g., a glutamine, an alanine or an aspartic acid residue. In certain embodiments, the substituting amino acid is non-acidic. Such variant integrin polypeptides have impaired binding affinity for activation-dependent ligands, but not for activation-independent ligands.

The various variant integrin polypeptides of the invention can be derived from any integrin α subunit or any integrin α subunit. The variant integrin polypeptides preferably include a ligand-binding portion of an A-domain or an A-like domain.

The invention also features methods for identifying a compound that binds to a variant integrin polypeptide of the invention. Such screening methods can entail exposing the polypeptide to a test compound of interest and determining whether the compound binds to the polypeptide. Thus, the assay can be a simple binding assay (e.g., where binding of the compound is measured only in the absence of the ligand) or a competitive binding assay (e.g., where binding of the compound is measured in the presence of the ligand).

The invention also features both methods for identifying compounds that interfere with the binding of an integrin ligand to an integrin and methods for identifying compounds that enhance binding of an integrin ligand to an integrin. The methods entail measuring the binding of an integrin ligand to a variant integrin polypeptide in the presence and absence of a test compound. The ability of a test compound to interfere with or enhance the binding of an integrin ligand to an integrin may also be tested. In addition, the binding specificity of a compound can be assessed by measuring the binding of the integrin ligand to a second integrin (or measuring the binding of a second ligand to the integrin) in the presence and absence of the test compound.

The invention also features methods for interfering with the binding of an integrin to an integrin ligand by administering a variant integrin polypeptide of the invention or an antibody that selectively binds to a variant integrin polypeptide of the invention. For example, a variant CD11b α subunit with impaired binding is constructed by substituting glutamic acid at position 336 of SEQ ID NO:30 with any other amino acid, e.g., glycine, valine, alanine, leucine, isoleucine, proline, serine, threonine, phenylalanine, tyrosine, tryptophan, lysine, arginine, histidine, aspartate, asparagine, glutamine, cysteine, and methionine. Thus, in one embodiment, the polypeptide can include amino acids 144 to 336 of SEQ ID NO:30 with a substituted Glu at position 336. Similarly, the variant polypeptide can be a CD11a α subunit having the glutamic acid at position 335 of CD11a replaced with any other amino acid. For example, in another embodiment, the variant polypeptide can include amino acids 150 to 335 of CD11a α subunit wherein the glutamic acid at amino acid 335 has been replaced by an amino acid selected from, among others, glutamine, aspartic acid, and alanine.

A variant polypeptide of the invention lacking the important glutamic acid residue have impaired ability to bind to activation-dependent ligands, but unimpaired ability to bind to activation-independent ligands. Such variant polypeptides can be used to distinguish between compounds that are activation-dependent from activation-independent ligands.

The invention also features methods of administering a variant integrin polypeptide of the invention or an antibody that selectively binds to a variant integrin polypeptide of the invention for the purpose of identifying the presence of a ligand which binds to an active integrin. Such assays are useful for diagnosing inflammation, e.g., occult inflammation (e.g. abscess or an active atherosclerotic lesion). Thus, the variant polypeptides lacking the important glutamic acid residue can serve as a more sensitive means by which to detect the presence of an activation independent ligand with little or no interference from activation dependent ligands.

The invention further features nucleic acid molecules (e.g., mRNA and DNA) encoding a polypeptide of the invention or a polypeptide which includes a polypeptide of the invention. The invention also includes nucleic acid molecule encoding a fusion polypeptide comprising a polypeptide of the invention and a second polypeptide, e.g., an immunoglobulin constant domain.

Certain experiments described below concern the design of a preparation of a variant form of CD11b (an integrin α subunit) that is more active than the wild-type form of CD11b. Without being bound by any particular theory, it appears that, in solution, the amount of this variant subunit that is in the open (active) conformation is greater than for the corresponding wild-type form of the subunit.

Also described below are certain other experiments that concern the design of a preparation of a variant form of CD11b with an impaired ability to bind to activation-dependent ligands, but with no effect on the ability to bind activation-independent ligands.

Creation of the variant CD11b involves deletion or substitution of a particular Ile residue or a particular Glu residue. Deletion or substitution of the Ile residue confers a high affinity phenotype in isolated CD11b A domain as well as in the intact integrin. Moreover, the Ile-modified A-domain can be crystallized in the "open" conformation. Thus, without being bound by any particular theory, it appears that an Ile-based allosteric switch controls affinity and conformation in the integrin A-domain. Accordingly, variant, high affinity forms of other integrin α subunits (and β subunits) can be created by deleting or substituting the corresponding highly conserved Ile residue. On the other hand, deletion or substitution of the particular Glu residue confers an impaired affinity for activation-dependent ligands, but not for activation-independent ligands.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A and 1B depict surface representation of the CD11bA domain crystal structure in its "closed" (FIG. 1A) and "open" (FIG. 1B) states, with the C-terminal α7 helix outlined as a gray ribbon, the isoleucine (I316) residue in black. An arrow points to the MIDAS face. MIDAS and SILEN (socket for isoleucine) lie on almost opposite ends of the A-domain structure.

FIGS. 1C and 1D depict magnified face views of SILEN residues (I135, L164, I236, Y267, lying within 4 Å radius from I316) in the "closed" (FIG. 1C) and "open" (FIG. 1D) conformations. In the "closed" form (FIG. 1C), I316 side chain is wedged in SILEN; L312 is seen on top. L312 moves to cover SILEN in the "open" structure (FIG. 1D). FIGS. 1A-1D were built using GRASP (Barry Honig, Columbia University, NY).

In FIGS. 2E and 2g, the metal ion is shown in purple, and hydrogen bonds as dotted yellow lines.

FIGS. 3A-3J depict the results of functional analysis of 11bA$^{E-G}$ and 11bA$^{123-315}$ A-domains using BIAcore™ for recording the interactions of 11bA$^{E-G}$ (FIGS. 3A-3E) and 11bA$^{123-315}$ (FIGS. 3F-3J) with the activation-dependent ligands iC3b (FIGS. 3A and 3F), fibrinogen (FIGS. 3B and 3G) or CD54 (FIGS. 3C and 3H). All three ligands bound to 11bA$^{123-315}$, but not to 11bA$^{123-321}$. The observed differences in binding were not due to differences in protein concentration, as binding to the activation-independent ligands, NIF (FIGS. 3D and 3I) and mAb 904 (FIGS. 3E and 3J) were comparable. To quantitatively determine the affinity, various concentrations of the A domain peptides were used. The binding data were analyzed by linear transformation, giving dissociation constants (Kd, mean±SD, n=2) of 0.46±0.15 µM (for iC3b), 0.25±0.07 µM (for fibrinogen), and 0.22±0.04 µM (for CD54).

FIG. 9 depicts an alignment of the A domains of nine alpha integrin α subunits (CD11b (SEQ ID NO:21), CD11c (SEQ ID NO:22), CD11d (SEQ ID NO:23), CD11a (SEQ ID NO:24), alpha 11 (SEQ ID NO:25), alpha 10 (SEQ ID NO:26), alpha 1 (SEQ ID NO:27), alpha 2 (SEQ ID NO:28), and alpha E (SEQ ID NO:29)).

FIGS. 10A and 10B depict hypothetical models of the αA-integrin CD11b/CD18, with Glu320 in the "closed" and "open" states, respectively.

FIGS. 11A and 11B depicts western blots showing the presence of CD18 in anti-CD11b immunoprecipitates from 293 cells expressing WT or mutant CD11b/CD18.

FIG. 11C depicts histograms showing the relative binding of the anti-CD11b mAb 44a and the anti-CD18 mAbs (TS1/18, KIM185, and KIM127) to 293 cells expressing WT and mutant CD11b/CD18.

FIG. 11D depicts histograms showing relative binding of iC3b to WT and mutant CD11b/CD18 in $Ca^{2+}$+$Mg^{2+}$ (1 mM each) containing buffer, $Mn^{2+}$ (0.5 mM) containing buffer, or $Ca^{2+}$+$Mg^{2+}$ buffer containing the activating mAbs KIM127 or KIM185, and relative binding of NIF and mAb107 to WT and E320A in the $Ca^{2+}$+$Mg^{2+}$ buffer.

FIG. 12 depicts the complete immature CD11b α subunit including the signal sequence (SEQ ID NO: 30).

DETAILED DESCRIPTION

Example 1

Figure 1E:
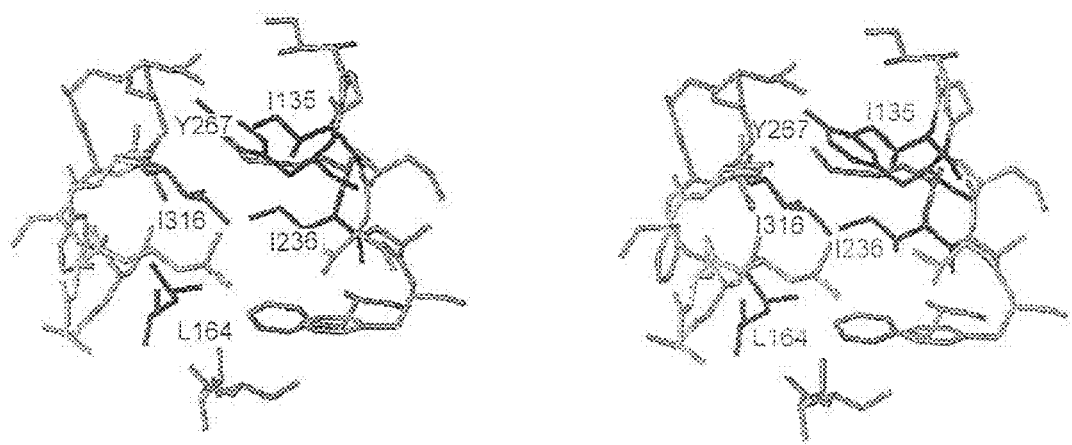
FIGS. 1E and 1F depict stereo views of the I316 coordination socket in the "closed" (FIG. 1E) and "open" (FIG. 1F) conformations. SILEN residues and I316 and L312 are labeled.

Generation of a Stable, High Affinity CD11b Variant A-Domain by Deletion

A variant CD11b A domain consisting of amino acids $E^{123}$ to $K^{315}$ of CD11b (11bA$^{123-315}$; also referred to as 11bA$^{E-K}$) was created. Note that the amino acid numbering in these examples references the numbering in the mature protein, while the amino acid numbering in Tables 2, 3, and 4, below, references the numbering in the complete immature protein (including signal sequence). CD11b has a 16 amino acid signal sequence. Thus, $E^{123}$ in the mature protein corresponds to $E^{139}$ in the complete immature protein and $I^{316}$ in the mature protein corresponds to $I^{332}$ in the complete immature protein. This variant 116A$^{123-315}$ domain was characterized and compared to a CD11b A domain consisting of amino acids $E^{123}$ to $G^{321}$ (11bA$^{123-321}$; also referred to as 11bA$^{E-G}$). A variant A domain with an Ile to Gly change at residue 316 (11bA$^{I \to G}$) was also created. All three proteins were expressed as GST fusion proteins that were cleaved to release the protein of interest.

The variant polypeptides were created using standard recombinant techniques. Restriction and modification enzymes were purchased from New England Biolabs, Inc. (Beverly, Mass.), Boehringer Mannheim (Germany), or GIBCO BRL (Gaithersburg, Md.). Site-directed mutagenesis was carried out in pGEX-4T-1 vector as described (Rieu et al. 1996 *J. Biol. Chem.* 271:15858). The following mutagenic primers were used: IFAdel Fwd: 5'-TATAGGATCCGAGGC-CCTCCGAGGGAGTCCTCAAGAGGATAG-3' (SEQ ID NO:18); Reverse: 5'-CTACTCGAGTTACTTCTC-CCGAAGCTGGTTCTGAATGGTC-3' (SEQ ID NO:19); I-G reverse: 5'-CTACTCGAGTTAACCCTCGATCG-CAAAGCCCTTCTC-3' (SEQ ID NO:20). Introduction of the respective mutation was confirmed by direct DNA sequencing. The PvuI-BspEI-restricted cDNA fragment of the A-domain containing the mutation was subcloned into the PvuI-BspEI-restricted CD11b cDNA, cloned into pcDNA3 plasmid, which containing full-length human CD11b (Rieu et al. 1996 *J. Biol. Chem.* 271:15858). 11b A$^{123-321}$ and 11bA$^{123-315}$ and 11bA$^{I \rightarrow G}$ A-domains were expressed as GST fusion proteins in *Escherichia coli* (Michishita et al. 1993 *Cell* 72:857), cleaved with thrombin and purified as described Li et al. 1999 *J. Cell Biol.* 143:1523. C$^{129}$ was replaced by S in all the expressed GST-A-domain fusion form to prevent formation of disulfide-linked dimmers in solution after thrombin cleavage (not shown). Purity was confirmed by SDS-PAGE analysis.

The structures of 11bA$^{123-321}$ and 11bA$^{123-315}$ were determined by x-ray crystallography. Crystals were grown using 10 mg/ml stock protein solutions and the hanging drop vapor diffusion method as described Li et al. (1998 *J. Cell Biol.* 143:1523). Several crystal conditions were tried for each A-domain. 11bA$^{123-315}$ and 11bA$^{I \rightarrow G}$ formed crystals in the presence of a reservoir solution containing 15% polyethylene glycol 8 K, 0.10 M Tris, pH 8.2, 150 mM CaCl$_2$, at room temperature. Crystals started to form within a week, grew to a typical size of 0.3 mm×0.05 mm×0.04 mm in two weeks, and belonged to the tetragonal space group P4, with unit cell of a=b=45.7 Å. 11bA$^{123-321}$ did not crystallize under these conditions, but formed crystals at room temperature using 10% polyethylene glycol 4000, 0.1M sodium citrate, pH 4.5, 5 mM MnCl$_2$ in the reservoir buffer. 11bA$^{123-321}$ was crystallized in the P2$_1$2$_1$2$_1$ space group with unit cell of a=48.1 Å, b=121.5 Å, c=74.5 Å.

A single 11bA$^{123-315}$ crystal was used to collect a 2.3 Å resolution data set, at 100 K, on beamline X12B of the National Synchrotron Light Source at the Brookhaven National Laboratory using a CCD detector. A single 11bA$^{123-321}$ crystal was used to collect a 2.6 Å resolution data set, at 100K, using in-house X-ray on image plate. DATA were processed with DENZO and SCALEPACK to an Rsym of 8.8%, 7.7%, respectively. The starting models were the refined 1.8 Å Mg$^{2+}$ structure (pdb accession code 1ido) (Lee 1995 *Cell* 80:631) comprising residues D132 to K315, and the refined 2.0 Å Mg$^{2+}$-structure (pdb accession code 1jlm) (Lee et al. 1998 *Structure* 6:923), comprising residues D132 to A318, with the metal and water molecules removed, respectively. The preliminary rigid body refinements were performed using X-plor, with the diffraction data range from 8.0 to 3.0 Å resolution with 5% of reflections for R-free calculation. The phases were gradually extended to high resolution and the structures were refined by several cycles of alternating torsion-angle dynamics and restrained individual isotropic B factor refinement protocols with all diffraction data between 8.0 and 2.6 Å, and 8.0 and 2.3 Å resolution, for 11bA$^{123-321}$ and 11bA$^{123-315}$ structures, respectively (Table 1). Model inspection and manual adjustments were made on SGI graphics workstations using O (Jones et al. 1991 *Acta Crystallogr.* 47:110). The addition of solvent molecules was based on the suitable peaks in difference maps, reasonable hydrogen bond and refined temperature factors of less than 50 Å$^2$. The addition of solvent molecules was based on the suitable peaks in difference maps, reasonable hydrogen bond and refined temperature factors of less than 50 Å$^2$. The structure was refined to a final R factor of 20.3% (R-free: 25.6%) for the 11bA$^{123-315}$ structure, and 21.9% (R-free: 30.0%) for the 11bA$^{123-321}$ structure. The final models comprises all nonhydrogen atoms of residues D132 to K315, 30 water molecules, and one Ca$^{2+}$ ion for 11bA$^{123-315}$, and residues D132 to G321, 44 water molecules and one Mn$^{2+}$ ions for 11bA$^{123-321}$. Crystallographic data is presented in Table 1.

TABLE 1

|  | 11bA$^{123-321}$ | 11bA$^{123-315}$ | 11bA$^{I316 \rightarrow G}$ |
|---|---|---|---|
| Space group | P2$_1$2$_1$2 | P4$_3$ | P4$_3$ |
| Unit cell constants (Å) | a = 48.1, b = 121.5, c = 74.6 | a = b = 45.7, c = 94.8 | a = b = 45.2, c = 95.0 |
| No. of unique reflections | 13,990 | 7,955 | 3,749 |
| Resolution (Å) | 8.0-2.6 | 8.0-2.3 | 8.0-3.0 |
| R$_{merge}$ (%)* | 7.7 {23}$^\S$ | 8.8 {28}$^\S$ | 11.2 {30.4}$^\S$ |
| Completeness (%) | 99.3 {98.4}$^\S$ | 91.1 {80.8}$^\S$ | 95.3 {73.6}$^\S$ |
| Redundancy | 5.9 | 2.3 | 2.7 |
| R-factor$^1$ (%) | 21.9 | 18.8 | 20.8 |
| R-free$^\ddagger$ (%) | 30.0 | 24.8 | 28.8 |
| Solvent molecules | 82 | 62 | 20 |
| Metal ions | 2 (Mn) | 1 (Ca) | 1 (Ca) |
| Root mean square (rms) deviations from ideal values |  |  |  |
| Bond lengths (Å) | 0.007 | 0.007 | 0.006 |
| Bond angle (°) | 1.3 | 1.3 | 1.25 |

*R$_{merge}$ = Σ|I − <I>|/ΣI where I is the observed intensity and <I> is the average intensity from multiple observations of symmetry-related reflections.
$^\S$Numbers in { } shows values for highest 0.1 Å resolution bin.
$^1$R-factor = Σ| Fo − Fc|Σ Fo.
$^\ddagger$R-free = Σ$_T$| Fo − Fc|Σ$_T$Fo, where T is a test set containing a randomly selected 5% of the reflections omitted from the refinement.

Figure 2A:
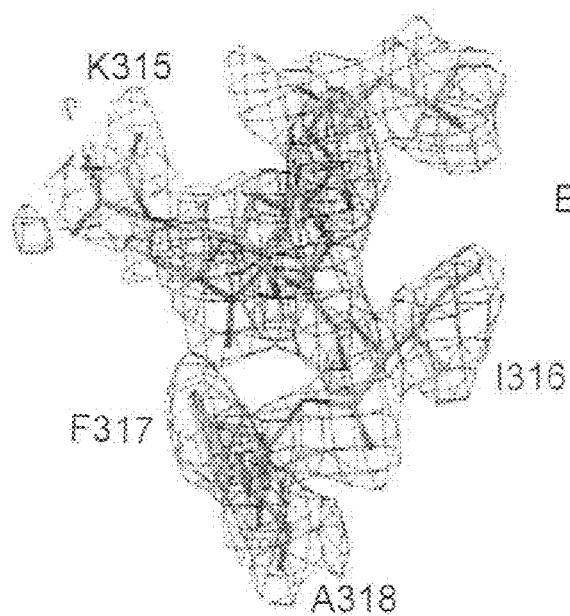
FIGS. 2A and 2B depict $2F_0$-$F_C$ electron density maps of the C-terminal portions of α7 from 11bA$^{123-321}$ (FIG. 2A) and 11bA$^{123-315}$ structures. The maps were contoured at 1.1σ, and made with O.
Figure 2B:
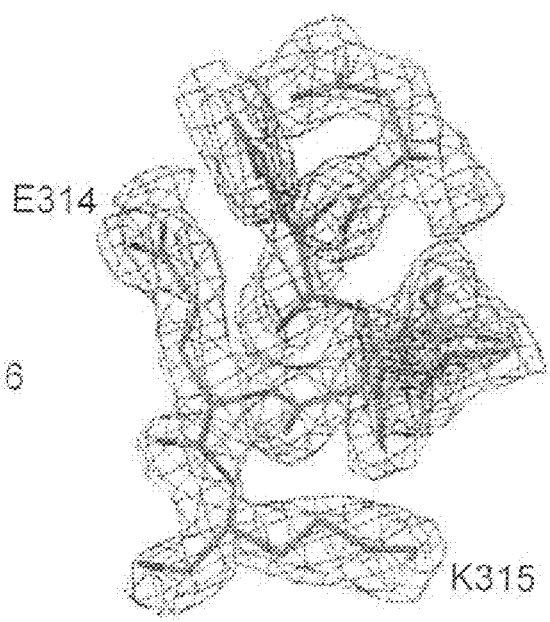
Figure 2C:
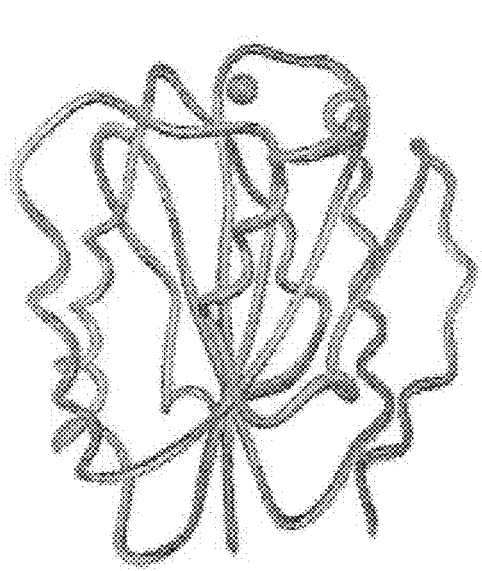
FIGS. 2C and 2D depict ribbon diagrams showing the complete superimposition of the 11bA$^{123-321}$ (FIG. 2C, red tracing) and 11bA$^{123-315}$ (FIG. 2D, red tracing) structures on the reported "closed" (FIG. 2C, green tracing) and "open" (FIG. 2D, green tracing) forms of the CD11b A domain, respectively. The metal ion is shown as a purple sphere.
Figure 2D:
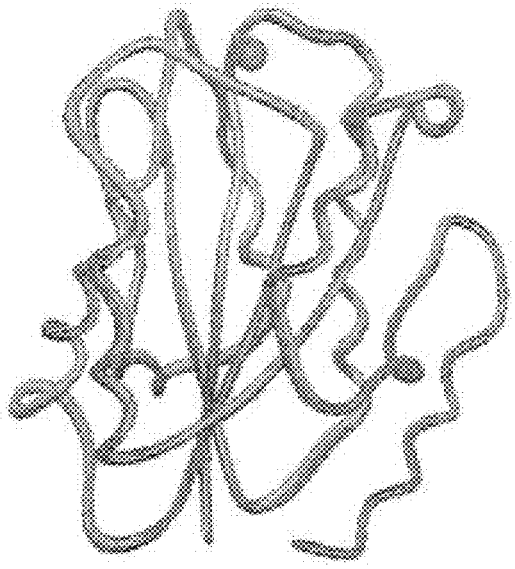
Figure 2E:
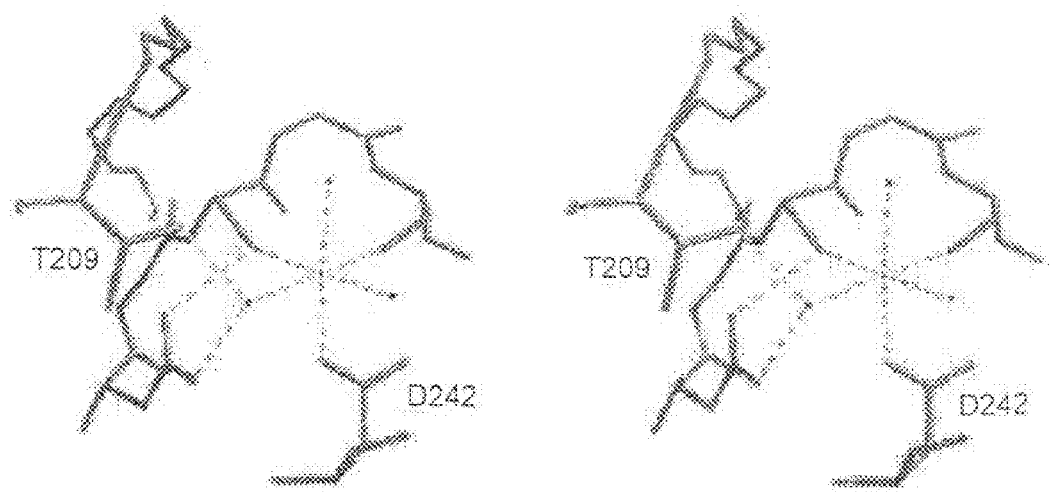
FIGS. 2E and 2F depict stereo views of MIDAS in the 11bA$^{123-321}$ (FIG. 2E) and 11bA$^{123-315}$ (FIG. 2F) structures. The direct D242-metal bond, and indirect T209-water-metal bond (FIG. 2E) are characteristic of the "closed" conformation. The meta lion in this case is $Mn^{2+}$. The MIDAS conformation (a direct T209-metal bond, indirect D242-water-metal bond, and a pseudo ligand glutamate, occupying the active site, shown in green, and directly coordinating the metal ion ($Ca^{2+}$) are those of the "open" conformation).
Figure 2F:
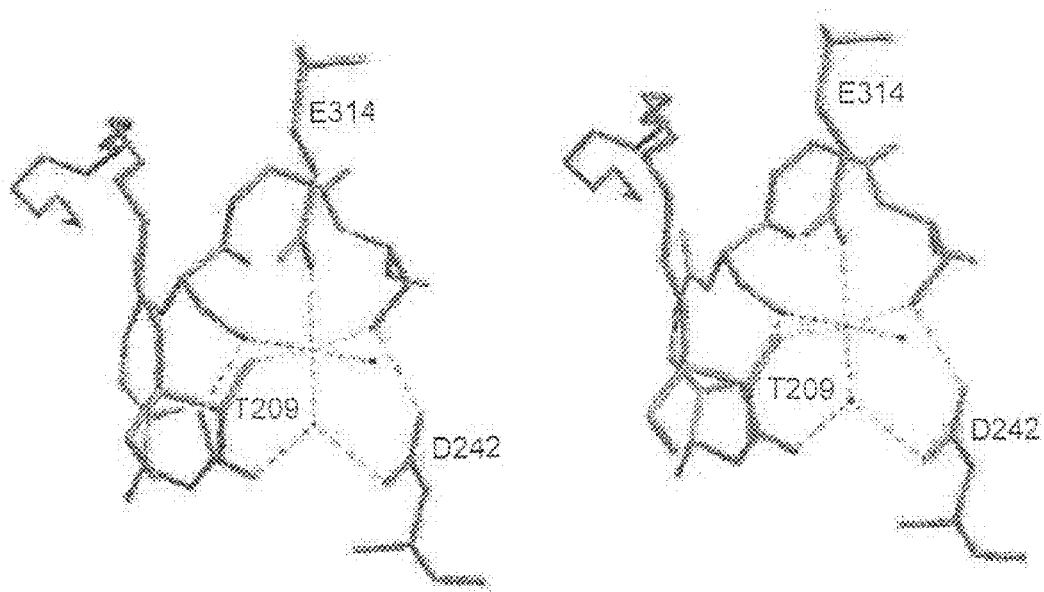

The crystal structure 11bA$^{123-321}$ was that of the "closed" conformation (FIGS. 2A, 2C, and 2E). In contrast, 11bA$^{123-315}$ crystallized in the "open" form (FIGS. 2B, 2D, and 2F).

The ligand binding properties of 11bA$^{123-321}$ and 11bA$^{123-315}$ were determined using surface plasmon resonance as previously described (Li et al., supra) on a BIAcore (BIAcore AB, Uppsala, Sweden). IC3b, fibrinogen or CD54 each was covalently coupled via primary amine groups to the dextran matrix of a separate CM5 sensor chip (BIAcore AB). BSA immobilized in the same way was used as a control surface. 11bA$^{123-321}$, 11bA$^{123-315}$ and 11bA$^{I \rightarrow G}$ A-domains were: flowed over the chip at 5 ml/min at different times. TBS (20 mM Tris-HCl, pH 8.0, 150 mM NaCl) with 2 mM MgCl$_2$ and 0.005% P20 (BIAcore AB) was used as the running buffer. 1 M NaCl in 20 mM Tris-HCl, pH 8.0, was used to remove the bound proteins and to regenerate the surface. Binding was measured as a function of time. The binding data (after subtracting background binding to BSA-coated chip) were analyzed using Scatchard plots as described (Dall'Acqua et al. 1996 *Biochemistry* 35:9667-9676). COS M7 simian fibroblastoid cells at ~70% confluence were transfected with supercoiled cDNAs encoding WT or CD11b$^{I \rightarrow G}$ together with full-length CD18 as described (Michishita et al., supra).

Transfected COS cells were grown for 24 h in Iscove's modified Dulbecco's medium (BioWhittaker, Inc., Walkersville, Md.) supplemented with 10% FBS, 2 mM glutamine, 50 IU/ml penicillin and streptomycin at 37° C. Cells were washed, detached with 0.1% trypsin-EDTA, and seeded in replicates for 24 h onto 24- or 48-well plates (Costar Corp., Cambridge, Mass.) or 100-mm petri dishes. Confluent monolayers in 24- or 48-well plates were used for cell-surface antigen quantification and ligand-binding studies, and those on petri dishes for immunoprecipitation studies. Heterodimer formation and binding of iC3b-coated erythrocytes to wild type and CR3$^{I \rightarrow G}$ holoreceptors were carried out as described (Rieu et al. 1996 *J. Biol. Chem.* 271:15858). Specific binding of iC3b to the holoreceptors was obtained by subtracting background binding to mock-transfected COS cells. Binding to CR3$^{I \rightarrow G}$ was expressed as a percentage of binding to wild type, after correcting for the degree of surface expression using binding of mAb904 (Rieu et al. 1996 *J. Biol. Chem.* 271:15858).

As shown in FIGS. 3A-3J, 11bA$^{123-321}$ showed no binding to the activation-dependent "physiologic" ligands, complement iC3b, firbrinogen and CD54 (ICAM-1). In contrast, 11bA$^{123-315}$ displayed high affinity binding to all three ligands (FIGS. 3A-3J). Both domains bound equally well to the activation-independent "ligands" NIF (neutrophil inhibitory factor) (FIGS. 3D, and 3I), and mAb 904 (FIGS. 3E and 3J), indicating that the differences observed are not caused by variations in A-domain concentrations. These data conclusively establish that the "open" and "closed" crystal structures correspond respectively to the "high" and "low" affinity states of integrin 11bA.

Example 2

Generation of a Stable, High Affinity State CD11b Variant by Substitution

Figure 4A:
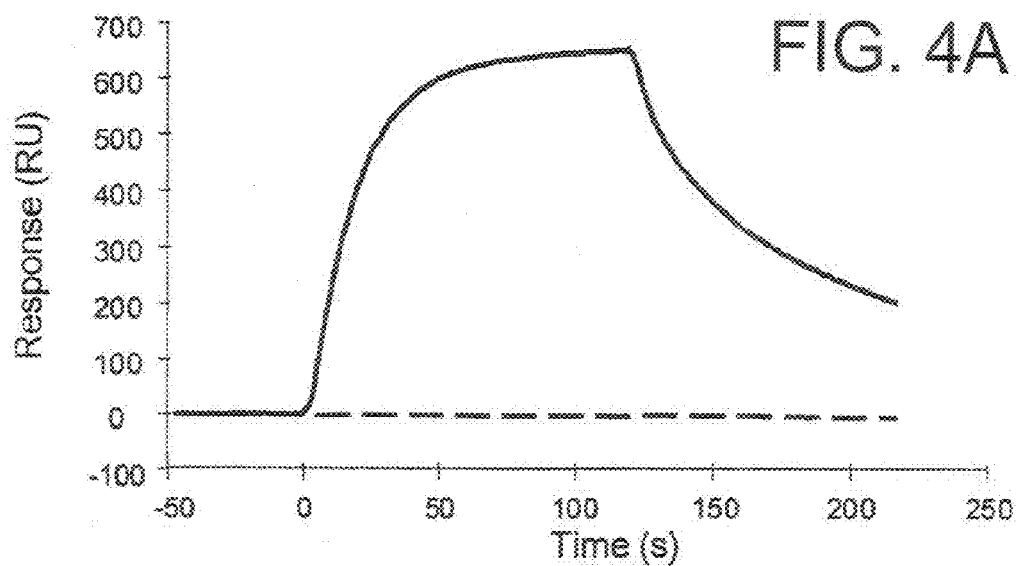
FIG. 4A depicts the results of an analysis of the binding of 11bA$^{1 \to G}$ to iC3b. The dotted line represents the lack of binding of 11bA$^{123-321}$ to the same ligand. The calculated Kd is 0.66±0.3 µM (mean±SD, n=2).
Figure 4B:
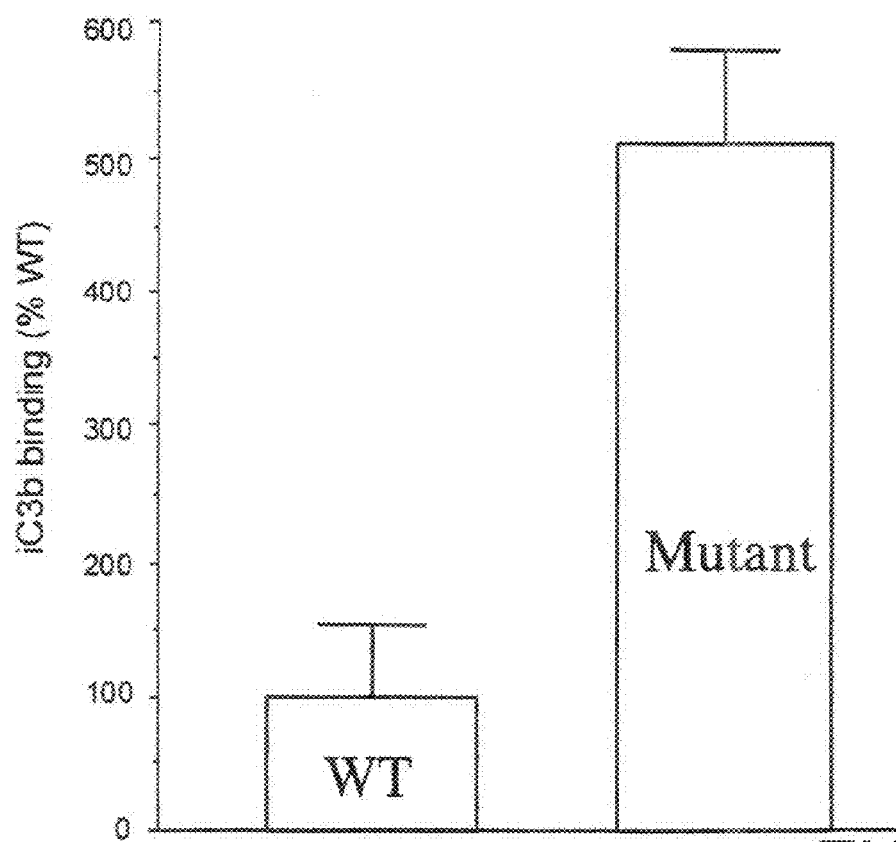
FIG. 4B depicts a histogram (mean±SD, n=3) showing the relative binding of $^{1 \to G}$ CR3 expressed on COS cells to iC3b, compared with wild-type receptor.
Figure 5:
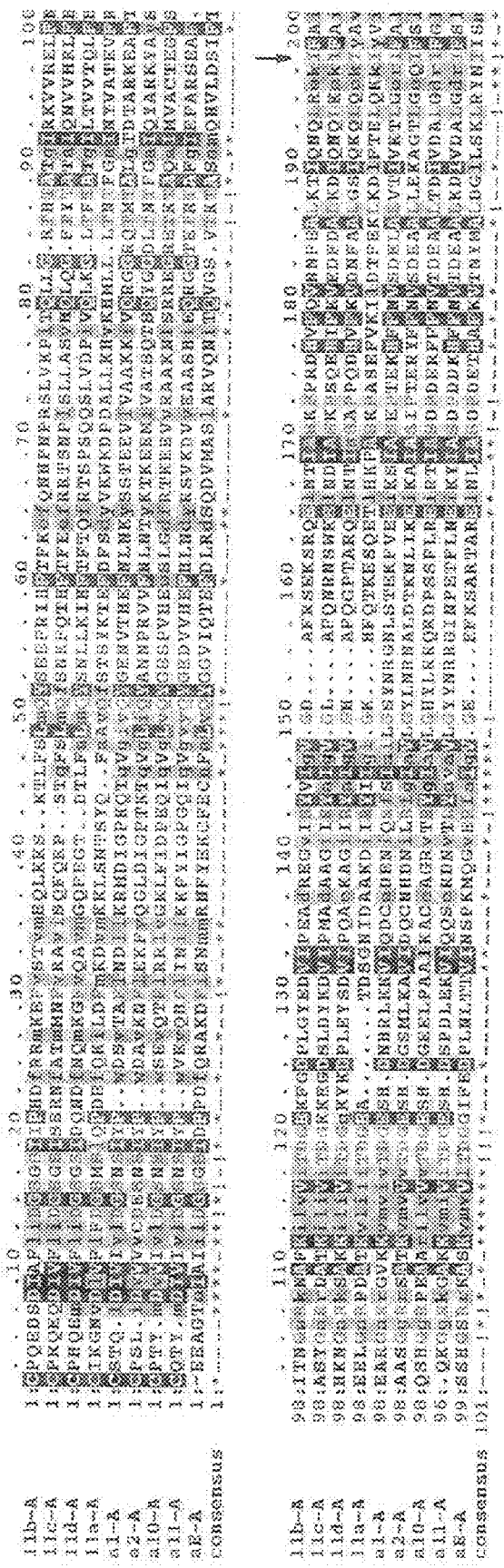
FIG. 5 depicts an alignment of the A domains of nine alpha integrin α subunit (CD11b (SEQ ID NO:1), CD11c (SEQ ID NO:2), CD11d (SEQ ID NO:3), CD11a (SEQ ID NO:4), alpha 1 (SEQ ID NO:5), alpha 2 (SEQ ID NO:6), alpha 10 (SEQ ID NO:7), alpha 11 (SEQ ID NO:8), and alpha E (SEQ ID NO:9)). In this alignment, the invariant Ile (I316) is indicated by an arrow.

Ile$^{316}$ is invariable in all integrin alpha A-domains cloned to date (FIG. 5). An A-domain with an Ile to glycine substitution (11bA$^{I \rightarrow G}$) exhibited a "high affinity" state (FIG. 4A). The same substitution created in the holoreceptor dramatically increased its ligand binding activity (FIG. 4B). The crystal structure 11bA$^{I \rightarrow G}$ was identical to that of the "open" 11bA$^{123-315}$ form. These data firmly establish that the "open" high affinity conformation is primarily dictated by an Ile-based switch, intrinsic to the domain, and acting allosterically to regulate ligand binding affinity on the MIDAS face. It is known that the inactive and active conformers of an integrin exist in the absence of ligand (Smith et al., supra; Yan et al. *J. Biol. Chem.* 275:7249-60, 2000). Based on the results described above, it appears that the role of the ligand is not in initiating the high affinity state as has been recently proposed (Emsely et al., supra), but in stabilizing it, through shifting the equilibrium between the low and high affinity state in favor of the latter (Li et al., supra). Integrin activation by inside-out signaling would lead to a shift in this equilibrium, increasing the proportion of high affinity receptors on the cell surface that become "available" for ligand binding. Ligand engagement would then generate new epitopes, perhaps extrinsic to the A-domain, that initiate outside-in signaling.

Figure 1F:
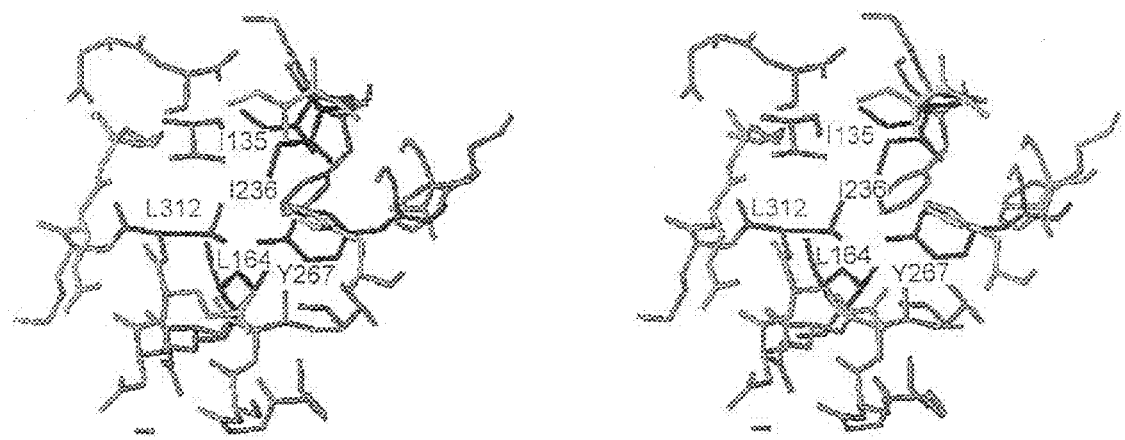

A conserved hydrophobic intramolecular socket (SILEN, Socket for Isoleucine), fastens the I$^{316}$ finger in the "closed" conformation; I$^{316}$ is replaced by L$^{312}$ in the "open" structure (FIGS. 1A and 1F). SILEN is formed by the hydrophobic side chains of I$^{135}$, L$^{164}$, I$^{236}$, and Y$^{267}$ both in the "closed" and "open" conformations. (FIGS. 1C and 1D). In several integrins, certain mutations that lie outside MIDAS produce gain-of function effects in the holoreceptor, and are believed to act allosterically (Zhang et al., supra; Oxvig et al., supra; Zhang et al., supra). These studies were carried out in the holoreceptors, making it difficult to provide a mechanistic interpretation, because of potential interdomain interactions and/or other quaternary effects. These mutations occur in or around SILEN. For example, substitution of the α1-βB loop of CD11b with that of CD11a, generates a constitutively active integrin (Zhang et al., supra). This region spans one of the SILEN residues L$^{164}$. Integrin activation also occurs in an L$^{164}$-F substitution (Oxvig et al., supra), which predictably makes SILEN smaller and, therefore, less accommodating to I$^{316}$. Other activating mutations involving E$^{131}$, D$^{132}$, K$^{231}$ and F$^{234}$ lie at the bottom of the structure, in close proximity to SILEN (Oxvig et al., supra), and may thus exert their effect through interference with the proper coordination of the Ile "finger" in SILEN. The inhibitory effect of certain mAbs with epitopes on the opposite side of MIDAS (e.g., mAb 44a, the epitope of which spans residues on the top of SILEN) may similarly be explained through stabilization of the SILEN pocket.

The presence of the N-terminal extension facilitates A-domain switching into the less favored high-affinity state (Li et al., supra). The underlying structural basis for this effect is unknown, since none of the residues in the N-terminal extension are included in the derived 3-D structures. It has been observed however that residues within this extension regulate ligand binding in A-domains. First, naturally occurring point mutations in this segment of the vWF A1 domain cause gain-of-function phenotypes in patients with type IIB vWf disease (Matsushita et al. 1995 *J. Biol. Chem.* 279:13406-14). This region also contains an activating mutation in CD11b A domain (Oxvig et al., supra). Third, synthetic peptide from the N-terminal extension inhibited CD11a-dependent adhesion. Structural data from the CD49b A-domain also show that three residues that extend beyond the α7 helix can pack into a crevice formed in part by residues in the N-terminal extension, bringing the N and C termini into very close proximity (Emsley et al., supra). Flexibility of the C-terminal residues in α7 has also been observed in the crystal and NMR structures of the CD11a A-domain. Taken together, these data suggest the N-terminal extension may offer an alternative by imperfect "competitive" surface for luring Ile away from SILEN, allowing some molecules to exist in the "open" form. The present data suggest that such a mechanism may operate in the holoreceptor, providing a mechanistic basis for integrin activation by inside-out signals.

Example 3

Generation of a CD11b Variant A-Domain Having Impaired Binding

In response to "inside-out" activation, ligand binding to integrins is mediated by αA, if present, and by βA, if not. In both instances, a ligand-derived acidic residue binds at MIDAS of αA or βA (Michishita et al., supra; Xiong et al. *Science* (Published online Mar. 7, 2002, Science Express); Lee et al. 1995 *Cell* 80:631-638). Similar outside-in signals are generated in response. The shared inside-out and outside-in signaling features in αA-containing and αA-lacking integrins suggest a common pathway of activation and signaling. Based on the structure of the ligand-binding site in the αA-lacking integrin αVβ3 (Xiong et al., supra) and the known structure-activity relationships in αA (Lee et al., supra; Emsley et al. 2000 *Cell* 100:47-56; Li et al. 1998 *J. Cell Biol.* 143:1523-1534; Huth et al. 2000 *Proc. Nat'l Acad. Sci. USA* 97:5231-5236; Xiong et al. 2000 *J. Biol. Chem.* 275:38762-38767; Lu et al. 2001 *Proc. Nat'l Acad. Sci. USA* 98:2393-2398), it is suggested that αA serves as an endogenous ligand for βA (FIGS. 8A and 8B), providing an explanation for the shared features in stimulus-response coupling. In theory, βA mediates ligand binding in all integrins, either directly in αA-lacking integrins or indirectly in αA-containing variants.

Figure 8A:
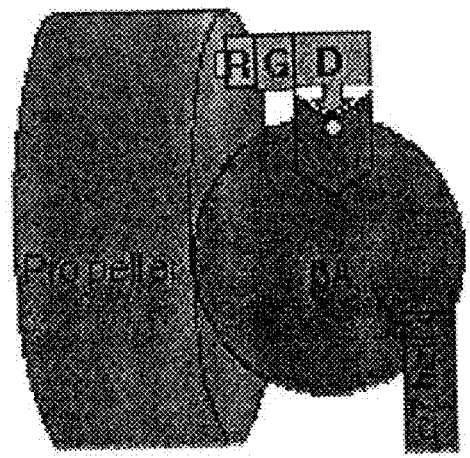
FIGS. 8A and 8B depict a cartoon representation of the α-subunit propeller and the β-subunit βA domains of an αA-lacking integrin and an αA-containing integrin, respectively.
Figure 8B:
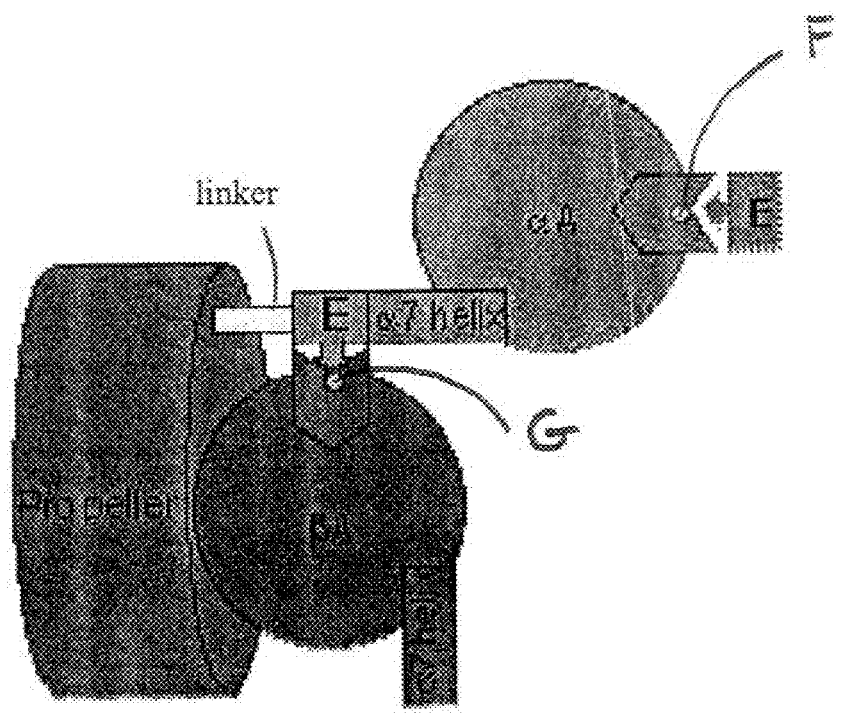

FIG. 8A shows a cartoon representation of an αA-lacking integrin head region, showing the α-subunit propeller and the β-subunit βA domains. The prototypical ligand RGD (Arg-Gly-Asp) contacts both subunits, with the Asp coordinating the metal ion in βA MIDAS and the Arg fitting into a pocket formed in part by residues from the propeller's D3-A3 loop. FIG. 8B shows a head region of an αA-containing integrin. αA projects from the D3-A3 loop in the propeller. In FIG. 8B, the metal ions at αA and βA MIDAS are indicated by the letters F and H, respectively. The C-terminal linker connects αA to the propeller. The N-terminal linker is not shown. The dotted box represents αA ligand Glu (E).

Three observations provide the basis for the theory that βA mediates ligand binding in all integrins, either directly in αA—lacking integrins or indirectly in αA—containing integrins. First and foremost, αA emerges from the propeller's D3-A3 loop, which forms part of the ligand-binding interface in αVβ3. Thus, the N- and C-termini of αA are expected to be very close to the βA MIDAS. Second, isolated αA mediates high-affinity interaction with physiologic ligands (Xiong et al. 2000 *J. Biol. Chem.* 275:38762-38767; Lu et al., supra). However, this interaction is regulated by βA in the holoreceptors, as mutations of βA MIDAS residues in β1, β2 or β3 integrins markedly reduce αA-mediated ligand binding and expression of activation-sensitive epitopes (Lu et al., supra; Goodman et al., supra; Puzon-McLaughlin et al. 1996 *J. Biol. Chem.* 271:20438-20443). Third, integrin ligands uniformly possess a flexible and solvent-exposed acidic residue that contacts the integrin through a metal ion (Xiong et al. Published online Mar. 7, 2002, Science Express; Lee et al., supra; Emsley et al., supra).

FIG. 9 shows the conservation of the invariant Glu in αA-integrins. The sequences of the human α-subunits were aligned with CLUSTALW 1.8. Shown in FIG. 9 is the C-terminal α7 helix of αA with the invariant Glu (indicated by an arrow) within a conserved tetrapeptide (sequence bracketed). The α7 helix in "closed" αA is underlined. Secondary structure-alignments of the cup tetrapeptide and the A4 strands of the propeller domain in the various integrins (underlined) are based on the crystal structures of αVβ3 and αA from CD11b (Lee et. al. 1995 *Structure* 3:1333-1340; Xiong et al. 2001 *Science* 294:339-345).

FIGS. 10A and 10B depict hypothetical models of the αA-integrin CD11b/CD18, showing $Glu^{320}$ in the "closed" (left) and "open" (active) (right) states of the αA domain, respectively. As αA switches from its inactive "closed" to its active "open" state, a 10 Å downward shift of α7 drastically alters the position of the invariant Glu relative to the βA MIDAS. It may be this shift that enables the Glu side chain to coordinate the metal ion in βA MIDAS in a manner similar to that of the ligand Asp in "liganded" αVβ3. The last three amino acids of the α7 helix extending into the linker sequence that includes the invariant Glu become disordered in the "open" form of αA and presumably flexible (Li et al. 1998 *J. Cell Biol.* 143:1523-1534; Xiong et al. 2000 *J. Biol. Chem.* 275:38762-38767; Lee et al. 1995 *Structure* 3:1333-1340), even in the context of the heterodimer (Lu et al., supra). In addition, the N- and C-terminal linkers flanking αA appear to be solvent-accessible, as they contain epitopes for function-blocking mAbs (Lu et al., supra; Binnerts et al. 1996 *J. Biol. Chem.* 271:9962-9968).

In FIG. 10B, the metal ions at βA MIDAS, ADMIDAS and LIMBS are indicated by the letters J, K, and L, respectively. The αA MIDAS metal is indicated by the letter M. FIG. 10A features βA in the "unliganded" state, and FIG. 10B shows βA in the "liganded" state. Two other combinations, αA "closed"+βA "liganded" and αA "open"+βA "unliganded," are also possible. No structural information is currently available on the linkers connecting the N- and C-termini of αA to the propeller, and thus the precise quaternary arrangements of αA will have to await experimental structural information. The present model was built in Modeller 4.0 (Sali et al. 1993 *J. Mol. Biol.* 234:779-815) using the αVβ3 structures and shows one possible location of αA that satisfies the geometric requirements dictated by the sequence alignment. Other possible arrangements remain consistent with the hypothesis. The C-terminal linker contains a second conserved Glu ($Glu^{333}$ in CD11b); however in this model, this residue is too distant from βA MIDAS and, therefore, unable to interact with it.

It is predicted that mutations of the invariant Glu will impair binding of αA-integrins to activation-dependent ligands without affecting their interaction with activation-independent ligands. The former condition has been established for CD11a/CD18 (Huth et al. 2000 *Proc. Nat'l Acad. Sci. USA* 97:5231-52.36). To evaluate the latter condition and the applicability of this prediction to other integrins, the role of the invariant Glu in integrin-ligand interactions was tested using another α-integrin CD11b/CD18. Substitutions of this Glu (Glu320 in mature CD11b) to Ala (E320A), Gln (E320Q) or Asp (E320D) were introduced, and the expression and function of the resulting receptors assessed in human 293 epithelial cells, which lack endogenous CD11b/CD18.

The mutations did not impair surface expression of CD11b/CD18 or heterodimer formation. FIGS. 11A and 11B depicts two western blots from experiments showing the presence of CD18 in anti-CD11b (using mAb 44a) immunoprecipitates from 293 cells expressing WT or mutant CD11b/CD18. Arrowheads indicate molecular weight markers at 20.5 kDa, 97.4 kDa, and 68 kDa. Each sample was run in duplicate and probed with 44a or anti-CD18 mAbs (Li et al. 1998 *J. Cell Biol.* 143:1523-1534). The upper part of the gel probed with mAb 44a (above dotted line) and the lower part of the duplicate gel probed with polyclonal anti-CD18 are shown. No CD18 was seen in anti-CD11b immunoprecipitates from mock-transfected 293 cells (Mock).

The mutant and wild type (WT) receptors also reacted equally well with mAbs KIM185 and KIM127. mAbs KIM185 appears to be an activating antibody (i.e. induces the switch to high affinity), while mAbs KIM127 is an activation-sensitive antibody (i.e. bind to the active form of the receptor). FIG. 11C depicts histograms showing the relative binding of the anti-CD11b mAb 44a, and the anti-CD18 mAbs (TS1/18, KIM185 and KIM127) to 293 cells expressing wild-type (WT) and mutant CD11b/CD18. Binding was normalized to that of the anti-CD11b mAb 903 (which binds outside αA) as previously described (Li et al., supra), which recognize regions within the CD18 leg segment.

FIG. 11D depicts histograms showing the relative binding of activation-dependent physiologic ligand iC3b to WT and mutant CD11b/CD18 in $Ca^{2+}+Mg^{2+}$ (1 mM each) containing buffer, $Mn^{2+}$ (0.5 mM) containing buffer, or $Ca^{2+}+Mg^{2+}$ buffer containing the activating mAbs KIM127 or KIM185. The histograms also show relative binding of NIF and mAb107 to WT and E320A in the $Ca^{2+}+Mg^{2+}$ buffer. All histograms show the mean±SD of quadruplet determinations from a representative experiment (one of 3 performed). The methods used were as described in Li et al., supra, except that 293 cells were transfected and attached to poly-L-lysine coated plastic wells before performing the various binding assays. Binding of mAbs 24 (Goodman et al., supra), mAb 107 (Li et al. 2002 *J. Immunol.* 168:1219-1225; mAb107 is produced by a hybridoma cell line deposited on Jan. 26, 2011, in the American Type Culture Collection (10801 University Blvd. Manassas, Va. 20110-2209) and assigned Accession Number ATCC PTA-11614), and KIM127 and 185 (Lu et al. 2001 *J. Immunol.* 166:5629-5637) were done as described.

The histograms show the results of binding studies using ligand iC3b, which binds to the αA MIDAS face in native CD11b/CD18. Binding of E320A and E320Q receptors to iC3b was markedly reduced. The E320D mutation was better tolerated, suggesting that the charge of the amino-acid side chain is a key determinant of binding. Further activation of the E320A integrin by KIM185 or KIM127 mAbs increased its binding to iC3b, but with consistently lower levels than that of the WT integrin. Significantly, none of the three mutations affected binding to neutrophil inhibitory factor (NIF) and the ligand-mimetic mAb 107, both of which are activation-independent ligands that bind to CD11b MIDAS. The E320A receptor failed to express the activation and cation-sensitive epitope for mAb 24 (Dransfield et al. 1989 *EMBO. J.* 8:3759), which binds to βA when αA is locked in the "open" conformation (Lu et al. 2001 *Proc. Nat'l Acad. Sci. USA* 98:2393-2398). Loss of mAb 24 binding is also seen in alanine substitutions of the βA MIDAS residues in the same integrin (Goodman et al., supra). The mAb 24 binding data suggest that the proposed "glutamate bridge" linking αA to βA may also facilitate outside-in signaling. The fact that the E320A mutation does not completely abolish iC3b binding is not surprising, and is indicative of additional contacts of αA with βA, perhaps involving the conserved tetrapeptide and adjacent linker residues (Huth et al. 2000 *Proc. Nat'l Acad. Sci. USA* 97:5231-5236).

Variant Integrin Polypeptides

Figure 6:
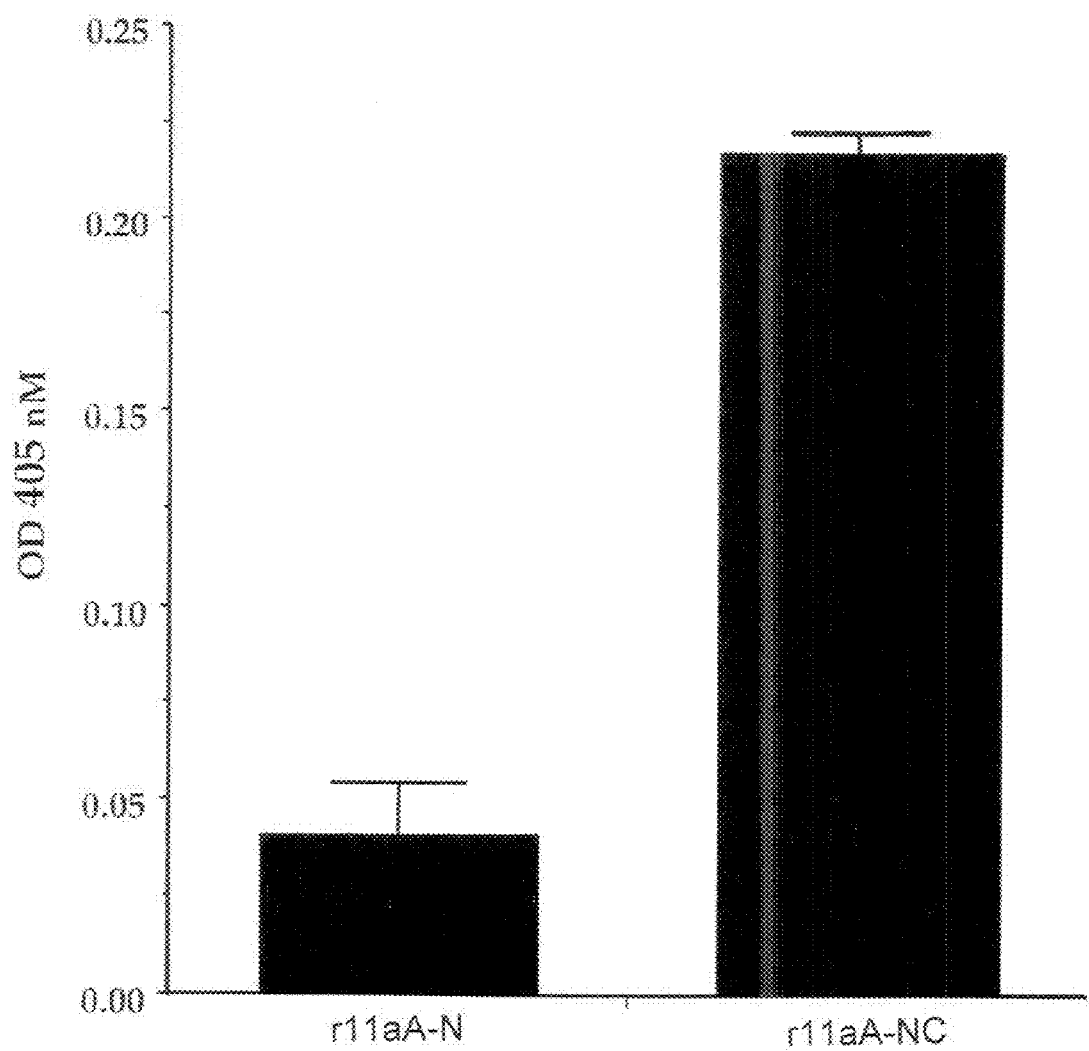
FIG. 6 shows that an I to G mutation of the invariant isoleucine in CD11a A domain induces an activated domain in this integrin, underscoring the applicability of the findings in the CD11b A domain to other integrin A-domains.

Given the sequence similarity among the A domains of integrin α subunits, deletion or substitution of the Ile in a selected integrin α subunit that corresponds to Ile$^{316}$ of CD11b should result in the creation of a variant integrin α subunit that is more active (i.e., in solution has a greater proportion of ligand binding form polypeptides) than the wild-type form of the subunit. FIG. 5 is an alignment of the C-terminal α7 helix of the A domains of nine integrin α subunits (CD11b, CD11c, CD11d, CD11a, alpha 1, alpha 2, alpha 10, alpha 11, and alpha E). In this alignment, the invariant Ile corresponding to Ile$^{316}$ of CD11b in the other integrin α subunits is outlined (arrow). Replacing the invariant Ile with Ala or Gly or some other suitable amino acid should create a variant integrin polypeptide with increased activity. We have shown this to be the case in the CD11a A-domain (FIG. 6). A variant CD11a A domain containing an I to G substitution displays binding to the activation-dependent ligand ICAM-1 in an ELISA assay. No binding was observed in the wild-type protein without this substitution. Alternatively, the portion of the integrin α subunit (or the A domain) that includes the invariant Ile and all amino acid residues C terminal to the invariant Ile can be deleted. Table 2 below lists the position of the invariant Ile in each of the integrin α subunits (relative to the immature protein sequence) depicted in FIG. 5.

TABLE 2

| Integrin α Subunit | GenBank Accession No. (GI No) | Invariant Ile Position in whole integrin | A domain |
|---|---|---|---|
| Human CD11b | RWHU1B (gi: 72063) | Residue 332 | C144-A334 |
| Human CD11c | RWHU1C (gi: 72064) | Residue 333 | C145-A335 |
| Human CD11d | AAB38547 (gi: 1167550) | Residue 332 | C144-A334 |
| Human CD11a | AAC31672 (gi: 2695574) | Residue 331 | C150-V333 |
| Human Alpha 1 (CD49a) | P56199 (gi: 2829468) | Residue 331 | C139-A333 |
| Human Alpha 2 (CD49b) | NP_002194 (gi: 4504743) | Residue 361 | C169-S363 |
| Human Alpha 10 | XP_002097 (gi: 17488936) | Residue 354 | C57-G251 |
| Human Alpha 11 | NP_036343 (gi: 19923397) | Residue 349 | C159-S351 |
| Human Alpha E | A53213 (gi: 1362834) | Residue 385 | E196-S387 |

The present invention features variant integrin α subunit polypeptides in which the invariant Ile (listed in Table 2) is substituted by Gly, Ala or some other amino acid (e.g., Val). The polypeptide can include part or all of the indicated A domain, e.g., 10, 20, 30, 40, 50, 60, 70, 80, 90, 100, 110, 120, 130, 140, 150, 160, 170, 180, 190, or 200 contiguous amino acids of the A domain that includes the position of the invariant Ile. The invention also includes variant integrin α subunits in which the Ile has been deleted. Also within the invention are polypeptides comprising the entire A domain of an integrin α except for the invariant Ile. For example, amino acids 144-132 of CD11b, amino acids 145-332 of CD11c, amino acids 144-331 of CD11d, amino acids 150-330 of CD11a, but does not include the remainder of the integrin α subunit. The invention also features polypeptides comprising the A domain of an integrin α subunit up to but not including the invariant Ile and further lacking the 5 amino acids following the invariant Ile (e.g., having amino acids 144-331, but not 332-336 of CD11b; having amino acids 145-332, but not 333-337 of CD11c; having amino acids 144-331, but not 332-336 of CD11d; having amino acids 150-330, but not 331-335 of CD11a; having amino acids 139-330, but not 331-335 of human alpha 1; having amino acids 169-360, but not 361-335 of human alpha 2; having amino acids 57-248, but not 249-253 of human alpha 10; having amino acids 159-348, but not 349-353 of human alpha 11; or having amino acids 196-384, but not 385-389 of human alpha E).

Figure 7:
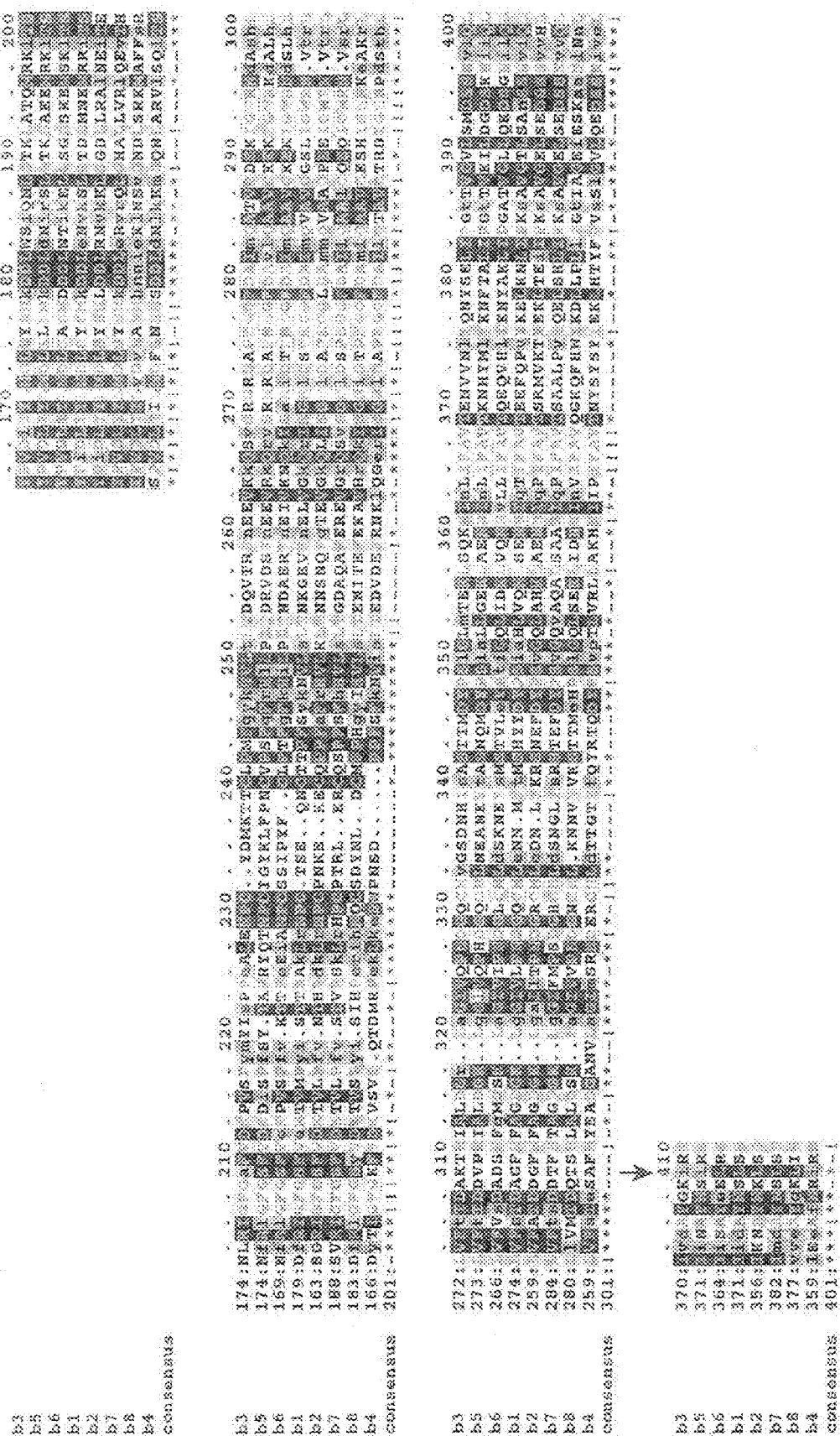
FIG. 7 is an alignment of the A-like domains of eight integrin β subunits (b3 (SEQ ID NO:10), b5 (SEQ ID NO:11), b6 (SEQ ID NO:12), b1 (SEQ ID NO:13), b2 (SEQ ID NO:14), b7 (SEQ ID NO:15), b8 (SEQ ID NO:16), and b4 (SEQ ID NO:17)). In this alignment, the residue corresponding to the invariant Ile in β subunits is indicated by an arrow.

Given the sequence similarity among the A-like domains of integrin β subunits, deletion or substitution of the Ile in a selected integrin β subunit that corresponds to Ile$^{316}$ of CD11b should result in the creation of a variant integrin β subunit that is more active (i.e., in solution has a greater proportion of ligand binding form polypeptides) than the wild-type form of the subunit. FIG. 7 is an alignment of the A-like domains of integrin β subunits. Replacing the conserved Ile with Ala or Gly or some other suitable amino acid should create a variant integrin polypeptide with increased activity. Alternatively, the portion of the integrin β subunit (or the A-like domain of the subunit) that includes the conserved Ile and all amino acid residues C terminal to the invariant Ile can be deleted. Table 3 below lists the position of the conserved Ile in each of the integrin β subunits depicted in FIG. 7.

TABLE 3

| Integrin β Subunit | GenBank Accession No. | Conserved Ile Position | A-like domain |
|---|---|---|---|
| Human β2(CD18) | P05107 (gi: 124966) | L363 | Y125-S365 |
| Human β1 | NP_002202 (gi: 19743813) | L378 | Y141-S380 |
| Human β3 | I77349 (gi: 2119640) | I377 | Y136-S379 |
| Human β4 | AAC51632 (gi: 2270923) | I366 | S128-S368 |
| Human β5 | A38308 (gi: 106776) | I378 | Y136-S380 |
| Human β6 | NP_000879 (gi: 9625002) | L371 | Y131-S373 |
| Human β7 | NP_000880 (gi: 4504777) | L389 | Y150-S391 |
| Human β8 | NP_002205 (gi: 4504779) | L384 | Y145-S386 |

The sequence similarity among the A domains of integrin α subunits also provides that deletion or substitution of the invariant Glu in a selected integrin α subunit that corresponds to Glu$^{320}$ of CD11b should result in the creation of a variant integrin α subunit that is less active than the wild-type form of the subunit to activation-dependent ligands, but not activation-independent ligands. FIG. 9 is an alignment of the C-terminal α7 helix of the A domains of nine integrin α subunits (CD11b (SEQ ID NO:21), CD11c (SEQ ID NO:22), CD11d (SEQ ID NO:23), CD11a (SEQ ID NO:24), alpha 11 (SEQ ID NO:25), alpha 10 (SEQ ID NO:26), alpha 1 (SEQ ID NO:27), alpha 2 (SEQ ID NO:28), and alpha E (SEQ ID NO:29)). Replacing the invariant Glu with Ala, Gln, or Asp, or some other suitable amino acid should create a variant integrin polypeptide with decreased activity to activation-dependent ligands. Table 4 below lists the position of the invariant Glu in each of the integrin α subunits depicted in FIG. 9.

TABLE 4

| Integrin α Subunit | GenBank Accession No. (GI No.) | Invariant Glu Position in whole integrin |
|---|---|---|
| Human CD11b | RWHU1B (gi: 72063) | Residue 336 |
| Human CD11c | RWHU1C (gi: 72064) | Residue 337 |
| Human CD11d | AAB38547 (gi: 1167550) | Residue 336 |
| Human CD11a | AAC31672 (gi: 2695574) | Residue 335 |
| Human Alpha 1 (CD49a) | P56199 (gi: 2829468) | Residue 335 |
| Human Alpha 2 (CD49b) | NP_002194 (gi: 4504743) | Residue 365 |
| Human Alpha 10 | XP_002097 (gi: 17488936) | Residue 358 |
| Human Alpha 11 | NP_036343 (gi: 19923397) | Residue 353 |
| Human Alpha E | A53213 (gi: 1362834) | Residue 389 |

The present invention features variant integrin α subunit polypeptides in which the invariant Glu (i.e., the Glu corresponding to amino acid 336 in immature CD11b) is substituted by any amino acid, including Gln, Ala, or Asp. The polypeptide can include part or all of the indicated A domain and flanking regions, e.g., 10, 20, 30, 40, 50, 60, 70, 80, 90, 100, 110, 120, 130, 140, 150, 160, 170, 180, 190, or contiguous amino acids of the A domain and flanking regions that include the position of the invariant Glu. The flanking region can be 5, 10, 15, 20, or 30 amino acids on either side of the A domain. Therefore, the polypeptide can also include the conserved tetrapeptide and/or the adjacent linker residues (FIG. 9). The invention can also include variant integrin α subunits in which the Glu has been deleted. Also within the invention are polypeptides wherein the amino acids of the conserved tetrapeptide are substituted or deleted. At least one, two, three, or all four amino acid of the conserved tetrapeptide can be substituted with any other amino acid to impair binding. The amino acids of the linker region may also be substituted to impair binding. The invention also features polypeptides comprising the A domain of an integrin α subunit up to the conserved tetrapeptide and/or adjacent linker sequences.

Nucleic Acid Molecules Encoding Variant Integrin Polypeptides

The invention features isolated or purified nucleic acid molecules that encodes a variant integrin polypeptide, e.g., a full length variant integrin subunit or a fragment thereof (e.g., in which the invariant Ile or Glu is deleted or substituted), e.g., a biologically active variant integrin polypeptide.

In one embodiment, an isolated nucleic acid molecule of the invention includes the nucleotide sequence encoding amino acids 123-315 of the CD11b α subunit (SEQ ID NO:1) or a portion thereof. The nucleic acid molecules can include non-coding sequences or sequences encoding all or a portion of a protein other than an integrin.

In another embodiment, an isolated nucleic acid molecule of the invention includes a nucleic acid molecule which is a complement of the nucleotide sequence encoding amino acids 123-315 of the CD11b α subunit.

A nucleic acid molecule of the invention may include only a portion of the nucleic acid sequence of SEQ ID NO:1. For example, such a nucleic acid molecule can include a fragment which encodes all or a portion (e.g., an immunogenic or biologically active portion) or an integrin A domain or A-like domain.

Variant Integrin Polypeptides

The present invention also includes variant integrin polypeptides. Such polypeptides can be produced using recombinant DNA methods, by chemical synthesis or using other techniques. The polypeptides can be used as immunogens or antigens generate antibodies which bind the active form of an integrin A-domain or A-like domain. The polypeptide can be post-translationally modified, e.g., glycosylated.

A variant integrin polypeptide can be part of a fusion protein which includes all or a portion of a second polypeptide that is not a variant integrin polypeptide. This second polypeptide can be fused to the C-terminus or the N-terminus of the variant integrin polypeptide. All or part of a third peptide may also be present. Thus, a variant integrin polypeptide can be fused to, e.g., GST, an immunoglobulin constant region, a heterologous signal sequence.

The variant integrin polypeptide fusion proteins of the invention can be incorporated into pharmaceutical compositions and administered to a subject in vivo. For example, the variant integrin polypeptides can be used to reduce skeletal muscle injury. Isolated CD11b A domain has already been found to reduce damage in an animal model of this type of injury. Briefly, purified recombinant rat CD11b A-domain was administered intravenously in a single dose (1 mg/kg) to seven groups of Lewis rats (5 per group), 30 minutes before inducing mechanically skeletal muscle injury. Equal numbers of rats were treated with a function-blocking anti-CD11b/CD18 mAb (1 mg/kg). Quantitative histological examination of the wounded area in controlled rats (treated with PBS), showed edema, myofiber disruption, necrosis and erythrocytes extravasation. Influx of neutrophils was detected 30 minutes post wound, followed by a second wave 3 hours later. There was also significant tissue necrosis outside the immediate wounded area (5 mm zone) associated with the presence of activated neutrophils. A-domain or mAb-treated rats showed a comparable and significant decrease in the number of infiltrated PMN (75±10%, n=35) and a protection of the muscular fibers outside the immediate zone of necrosis (80±8%, n=35). These data show that the A-domain can be an effective tissue-preserving agent in this model of muscular injury. Variant A domain should be equally effective.

The variant integrin polypeptide fusion proteins can be used to affect the bioavailability of a variant integrin polypeptide ligand.

Variant integrin polypeptide fusion proteins may be useful therapeutically for the treatment of disorders caused by, for example, ischemia-reperfusion injury (*Stroke* 30:134-9, 1999), immune complexes (*J. Exp. Med.* 186:1853-63, 1997), restenosis, and parasitic diseases (e.g. *Ancylostoma* spp; see *J. Cell Biol.* 127:2081-91, 1994).

Moreover, the variant integrin polypeptide-fusion proteins of the invention can be used as immunogens to produce anti-variant integrin polypeptide antibodies in a subject, to purify variant integrin polypeptide ligands and in screening assays to identify molecules that inhibit the interaction of variant integrin polypeptide with an variant integrin polypeptide ligand.

Expression vectors are commercially available that already encode a fusion moiety (e.g., a GST polypeptide). A variant integrin polypeptide-encoding nucleic acid can be cloned into such an expression vector such that the fusion moiety is linked in-frame to the variant integrin polypeptide protein.

Variant integrin polypeptides can be produced using an expression vectors (e.g., a plasmid vector or a viral vector). The vector can be autonomously replicating or integrated in to the host genomes. The expression vector can include at least one regulatory sequence (e.g., promoter, enhancer, polyA site, or a cell- or tissue-specific transcription factor binding site) that is operatively linked to the nucleic acid sequence to be expressed. The expression vector can be designed for expression in prokaryotic or eukaryotic cells, e.g., plant cell, insect cells, yeast cells, mammalian cells, and *E. coli*. Depending on the host cells used to express the variant integrin polypeptide, it may be desirable to encode the polypeptide using codons optimized for the host cell. In some cases it may be desirable to employ an expression vector capable of directing tissue-specific expression.

The invention also features host cells or recombinant cells harboring a nucleic acid molecule encoding a variant integrin polypeptide. The nucleic acid molecule can be integrated into the host cells genome or present in an autonomously replicating vector. A host cell can be any prokaryotic or eukaryotic cell, e.g., *E. coli*, an insect cell, yeast or a mammalian cell. The nucleic acid molecules can be introduced into the host cells through transformation or transfection techniques.

A host cell of the invention can be used to produce (i.e., express) a variant integrin polypeptide by culturing the host cell under conditions such that the polypeptide is produced and then isolating the polypeptide from the cells or the culture medium.

Antibodies Recognizing Variant Integrin Polypeptides

The invention also features antibodies directed against a variant integrin polypeptide. Such antibodies bind to the variant polypeptide with greater affinity than they bind to the corresponding wild-type integrin polypeptide. The antibodies can be generated using standard methods and can be screened by comparing the binding of the antibody to the variant integrin polypeptide to binding of the antibody to the corresponding wild-type polypeptide.

The term "antibody" refers to an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin. The antibody can be a polyclonal, monoclonal, recombinant, e.g., a chimeric or humanized, fully human, non-human, e.g., murine, or single chain antibody. In a preferred embodiment it has effector function. The antibody can be coupled to a toxin or imaging agent for use in diagnosis of occult inflammation (e.g. in abscess or active atherosclerotic plaques).

Chimeric, humanized but most preferably, completely human antibodies are desirable for applications which include repeated administration, e.g., therapeutic treatment (and some diagnostic applications) of human patients.

The anti-variant integrin polypeptide antibody can be a single chain antibody which can be optionally dimerized or multimerized to generate multivalent antibodies. The antibody can be designed to have little or no ability to bind to an Fc receptor.

The antibodies of the invention can be used to detect or purify integrin subunits that are in the active conformation. Thus, they can be used to evaluate the abundance and pattern of expression of an active form of an integrin as part of a clinical testing procedure. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials (e.g., horseradish peroxidase, alkaline phosphatase, β-galactosidase, acetylcholinesterase, streptavidin/biotin and avidin/biotin, umbelliferone, fluorescein, fluorescein isothiocyanate, rhodamine, dichlorotriazinylamine fluorescein, dansyl chloride or phycoerythrin, luminol, luciferase, luciferin, aequorin, $^{125}$I, $^{131}$I, $^{35}$S and $^{3}$H).

Screening Assays to Identify Compounds that Interact with a Variant Integrin Polypeptide The invention features methods for evaluating a compound for the ability to bind to a variant integrin polypeptide or inhibit the ability of an integrin ligand (e.g., a naturally-occurring integrin ligand) to bind to a variant integrin polypeptide. The methods can include contacting the compound with the variant integrin polypeptide in the presence or absence of a ligand and measuring the ability of the compound or the ligand to bind to the variant polypeptide. Moreover, methods can include evaluating compounds that can enhance the binding of a ligand to an impaired variant integrin polypeptides or screen for or differentiate between activation-dependent ligands and activation-independent ligands.

The methods can be performed in vitro, e.g., in a cell free system, or in vivo, e.g., in a two-hybrid interaction trap assay. The method can be used to identify naturally-occurring molecules which interact with an integrin. It can also be used to find natural or synthetic inhibitors of the interaction between an integrin and an integrin ligand.

The compounds tested can be, e.g., proteins, peptides, peptidomimetics, peptoids, and small molecules. The test compounds can be obtained from combinatorial libraries including: biological libraries; peptoid libraries; spatially addressable parallel solid phase or solution phase libraries; synthetic library methods requiring deconvolution; "one-bead one-compound" libraries.

Libraries of compounds may be presented in solution (e.g., Houghten 1992 *Biotechniques* 13:412-421), or on beads (Lam 1991 *Nature* 354:82-84), chips (Fodor 1993 *Nature* 364:555-556), bacteria (Ladner U.S. Pat. No. 5,223,409), spores (Ladner U.S. Pat. No. 5,223,409), plasmids (Cull et al. 1992 *Proc. Nat'l Acad. Sci. USA* 89:1865-1869) or on phage (Scott and Smith 1990 *Science* 249:386-390; Devlin 1990 *Science* 249:404-406; Cwirla et al. 1990 *Proc. Nat'l Acad. Sci.* 87:6378-6382; Felici 1991 *J. Mol. Biol.* 222:301-310; Ladner, supra.).

The screening assay can be a cell-based assay in which a cell which expresses an variant integrin polypeptide protein or biologically active portion thereof is contacted with a test compound, and the ability of the test compound to modulate variant integrin polypeptide activity is determined. Determining the ability of the test compound to modulate variant integrin polypeptide activity can be accomplished by monitoring, for example, the ability to bind an integrin ligand.

The ability of the test compound to modulate variant integrin polypeptide binding to a compound, e.g., an integrin ligand or to bind to variant integrin polypeptide can also be evaluated. This can be accomplished, for example, by coupling the compound, e.g., the substrate, with a radioisotope or enzymatic label such that binding of the compound, e.g., the substrate, to variant integrin polypeptide can be determined by detecting the labeled compound, e.g., substrate, in a complex. Alternatively, a variant integrin polypeptide or the integrin ligand can be coupled with a radioisotope or enzymatic label to monitor the ability of a test compound to modulate variant integrin polypeptide binding to an integrin ligand. For example, compounds can be labeled with $^{125}$I, $^{35}$S, $^{14}$C, or $^{3}$H, either directly or indirectly, and the radioisotope-detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

In yet another embodiment, a cell-free assay is provided in which an variant integrin polypeptide or biologically active portion thereof is contacted with a test compound and the ability of the test compound to bind to the variant integrin polypeptide or biologically active portion thereof is evaluated. Preferred biologically active portions of the variant integrin polypeptide to be used in assays of the present invention include fragments that bind an integrin ligand.

Soluble and/or membrane-bound forms of isolated proteins (e.g., variant integrin polypeptide proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the variant integrin polypeptide protein to bind to a target molecule, e.g., an integrin ligand, can be accomplished using real-time Biomolecular Interaction Analysis (BIA) as described above (see, e.g., Sjolander and Urbaniczky 1991 Anal. Chem. 63:2338-2345 and Szabo et al. 1995 Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the polypeptide or the test compound is anchored onto a solid phase. The polypeptide/test compound complexes anchored on the solid phase can be detected at the end of the reaction. Preferably, the polypeptide can be anchored onto a solid surface, and the test compound, (which is not anchored), can be labeled, either directly or indirectly, with a detectable labels.

It may be desirable to immobilize either a variant integrin polypeptide, an anti-variant integrin polypeptide antibody or its target molecule to facilitate separation of complexed from uncomplexed forms of one or both of the proteins, as well as to accommodate automation of the assay. Binding of a test compound to a variant integrin polypeptide protein, or interaction of a variant integrin polypeptide protein with a target molecule-in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/variant integrin polypeptide fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or variant integrin polypeptide protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of variant integrin polypeptide binding or activity determined using standard techniques.

Other techniques for immobilizing either a variant integrin polypeptide or a target molecule on matrices include using conjugation of biotin and streptavidin. Biotinylated variant integrin polypeptide or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with variant integrin polypeptide or target molecules but which do not interfere with binding of the variant integrin polypeptide to its target molecule. Such antibodies can be derivatized to the wells of the plate, and unbound target or variant integrin polypeptide protein trapped in the wells by antibody conjugation. Methods for detecting such complexes, in addition to those described above for the GST-immobilized complexes, include immunodetection of complexes using antibodies reactive with the variant integrin polypeptide or target molecule, as well as enzyme-linked assays which rely on detecting an enzymatic activity associated with the variant integrin polypeptide or target molecule.

Alternatively, cell free assays can be conducted in a liquid phase. In such an assay, the reaction products are separated from unreacted components, by any of a number of standard techniques, including chromatography, electrophoresis and immunoprecipitation. In a preferred embodiment, the assay includes contacting the variant integrin polypeptide or biologically active portion thereof with a known compound which binds variant integrin polypeptide to form an assay mixture, contacting the assay mixture with a test compound, and determining the ability of the test compound to interact with an variant integrin polypeptide protein, wherein determining the ability of the test compound to interact with an variant integrin polypeptide includes determining the ability of the test compound to preferentially bind to variant integrin polypeptide or biologically active portion thereof, or to modulate the activity of a target molecule, as compared to the known compound.

To identify compounds that interfere with the interaction between a variant integrin polypeptide and an integrin ligand, a reaction mixture containing the variant integrin polypeptide and the ligand is incubated, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the variant integrin polypeptide and integrin ligand is then detected. The formation of a complex in the control reaction, but not in the reaction mixture containing the test compound, indicates that the compound interferes with the interaction. Additionally, complex formation within reaction mixtures containing the test compound and variant integrin polypeptide can also be compared to complex formation within reaction mixtures containing the test compound and the corresponding wild-type integrin polypeptide. These assays can be conducted in a heterogeneous or homogeneous format. Heterogeneous assays involve anchoring either the variant integrin polypeptide or the binding partner (i.e., the integrin ligand) onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the variant integrin polypeptides and the binding partner (e.g., an integrin ligand), e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the variant integrin polypeptide or the integrin ligand, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the variant integrin polypeptide and the integrin ligand is prepared in that either the variant integrin polypeptide or the integrin ligand is labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt variant integrin polypeptide-binding partner interaction can be identified.

In yet another aspect, the variant integrin polypeptide proteins can be used as "bait proteins" in a two-hybrid assay or three-hybrid assay (see, e.g., U.S. Pat. No. 5,283,317; Zervos et al. 1993 *Cell* 72:223-232; Madura et al. 1993 *J. Biol. Chem.* 268:12046-12054; Bartel et al. 1993 *Biotechniques* 14:920-924; Iwabuchi et al. 1993 *Oncogene* 8:1693-1696; and Brent WO94/10300), to identify other proteins, which bind to or interact with variant integrin polypeptide.

A two-hybrid assay can be carried out using a variant A domain as the bait protein. Briefly, the variant A domain is fused to the LexA DNA binding domain and used as bait. The prey is an aptamer library cloned into the active site loop of TrxA expression as a fusion protein with an N-terminal nuclear localization signal, a LexA activation domain, and an epitope tag (Colas et al. 1996 *Nature* 380:548; and Gyuris et al. *Cell* 1993 75:791). Yeast cells are transformed with bait and prey genes. If an aptamer binds to variant A domain, the LexA activation domain is brought into proximity with the LexA DNA binding domain and expression of genes having an appropriately positioned LexA binding site increases.

To test this system, yeast strain EGY48 was transformed with the bait plasmid and pSH18-34 (a URA3, 2 μm plasmid containing the GAL1 promoter fused to lacZ, in which the GAL1 enhancer-like Upstream Activating Sequence (UASG) has been replaced with binding sites for eight LexA dimers). The yeast strain contains two reporter genes, LexAop-LEU2

(replaces the yeast chromosomal LEU2 gene) and LexAop-lacZ, carried on a 2 μm HIS3+ plasmid). Transformed cells were plated on medium containing X-gal. The presence of the bait did not cause the expression of β-galactosidase. The bait by itself also did not activate the LexAop-Leu2 gene in EGY48, since the transformed cells did not grow on Leu deficient plates. Next, nuclear transport of the bait was assessed using the bait plasmid and a pJK101 reporter in a repression type assay. In this assay DNA binding by transcriptionally inert LexA fusion proteins can be detected. The pJK101 reporter is a URA3, 2 μm plasmid containing most of the UASG. A high affinity binding site for lexA is located between the Gall transcription start and the UASG. CD11bA-LexA bait impaired the galactosidase activity of yeast harboring the pJK101 plasmid when grown on galactose medium, indicating that this bait enters the nucleus.

An aptamer library was introduced into the Leu and lacZ reporter-containing yeast cells. Synthesis of library proteins was induced by growing the yeast in galactose medium. In the absence of a suitable prey that binds the bait, the yeast cells does not grow on Leu⁻ medium and have no β-galactosidase activity. A cell expressing a suitable prey will form colonies on Leu medium and have β-galactosidase activity. Selective galactose (but not glucose) inducible expression allows the Leu and LacZ phenotypes to be unambiguously ascribed to the library protein, diminishing the number of library plasmids that must be excluded by subsequent analysis. Plasmids from positive colonies (i.e., colonies able to grow on galactose, Ura⁻, Trp⁻ His⁻ Leu⁻ plates) were rescued (Hoffman et al. 1987 *Gene* 57:267). Before the respective clones were further characterized, the specificity of their interaction with the bait was tested. This was done by showing that they do not interact with unrelated or nonfunctional baits (e.g., a CD11a A-domain-lexA and 11bA-D242A-lexA respectively), with the DNA-binding domain portion of the bait or nonspecifically with the promoters or other elements of the transcription machinery. The library plasmids were rescued from the galactose-dependent Leu+ lacZ+ yeast and re-introduced into the original selection strain and into other strains containing different baits. Specific interactors confer the galactose-dependent Leu+ and lacZ+ phenotype to yeast containing the original bait, but not to yeast containing unrelated baits. An interaction mating assay can be used to test specificity. Briefly, a strain that contains the prey is mated with different yeast strains which express either the original bait protein or the control bait proteins. Reporters should only be active in diploids that contain the original bait (Finley et al. (1994) *Proc. Nat'l Acad. Sci. USA* 91:12980).

Screening assays involving the identification of a compound that binds to or activates a variant integrin of the invention can be combined with additional assay steps. Thus, the invention includes identifying a compound that binds to a variant integrin of the invention to identify a variant integrin binding compound and then assessing the ability of that compound to bind to the corresponding wild-type integrin (or a different variant integrin). Compounds that bind to a variant integrin can be screen for activity in an animal model of a process involving an intergrin. Examples of such models are described below.

It can be desirable to perform screening assays using cells expressing the both variant integrin and the corresponding subunit with which it normally form heterodimer. Thus, CD11a, CD11b, and CD11c could be expressed in a cell along with CD18.

This invention further pertains to novel agents identified by the above-described screening assays. Accordingly, it is within the scope of this invention to further use an agent identified as described herein (e.g., an variant integrin polypeptide modulating agent) in an appropriate animal model to determine the efficacy, toxicity, side effects, or mechanism of action, of treatment with such an agent. Furthermore, novel agents identified by the above-described screening assays can be used for treatments as described herein.

Pharmaceutical Compositions

The variant integrin polypeptides, fragments thereof, as well as anti-variant integrin polypeptide antibodies (also referred to herein as "active compounds") of the invention can be incorporated into pharmaceutical compositions. Such compositions typically include the protein or antibody and a pharmaceutically acceptable carrier. As used herein the language "pharmaceutically acceptable carrier" includes solvents, dispersion media, coatings, antibacterial and anti-fungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, intravenous, intradermal, subcutaneous, oral, inhalation, transdermal, transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions: in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining: the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indeces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration are often possible. Modifications such as lipidation can be used to stabilize antibodies and to enhance uptake and tissue penetration (e.g., into the brain). A method for lipidation of antibodies is described by Cruikshank et al. 1997 *J. Acquired Immune Deficiency Syndromes and Human Retrovirology* 14:193.

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin or a protein such as a cytokine or interleukin.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. 1994 *Proc. Nat'l Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Animal Models of Processes Involving Integrins

A model of vascular injury that can be useful in testing potential therapeutic compositions is described by Simon et al. 2000 *J. Clin. Invest.* 105:293). Tang et al. (1997 *J. Exp. Med.* 186:1853) describe CD11b knockout mice which can be useful in various screening assays. An animal model of burn injury may also be useful (*Plast. Reconstr. Surg.* 1995 96:1177).

Methods of Treatment

The present invention provides for both prophylactic and therapeutic methods of treating a subject at risk of (or susceptible to) a disorder or having a disorder associated with aberrant or unwanted integrin expression or activity.

"Treatment" or "treating a patient", as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, palliate, improve or affect the disease, the symptoms of disease or the predisposition toward disease. A therapeutic agent includes, but is not limited to, small molecules, peptides, antibodies, ribozymes and antisense oligonucleotides.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

What is claimed is:

1. A monoclonal antibody mAb107 produced by a hybridoma cell line deposited in the American Type Culture Collection under Accession Number ATCC PTA-11614 that binds specifically to integrin alpha subunit CD11b.

2. The monoclonal antibody of claim 1, wherein the antibody is recombinant.

3. The monoclonal antibody of claim 1, wherein the antibody is chimeric.

4. The monoclonal antibody of claim 1, wherein the antibody is humanized.

5. A composition comprising an immunologically active portion of monoclonal antibody mAb107 produced by hybridoma cell line deposited in the American Type Culture Collection under Accession Number ATCC PTA-11614 that binds specifically to integrin alpha subunit CD11b, comprising an F(ab) or F(ab')$_2$ fragment of monoclonal antibody mAb107.

\* \* \* \* \*

UNITED STATES PATENT AND TRADEMARK OFFICE
CERTIFICATE OF CORRECTION

PATENT NO. : 7,998,738 B2
APPLICATION NO. : 12/021074
DATED : August 16, 2011
INVENTOR(S) : M. Amin Arnaout, Rui Li and Jian-Ping Xiong It is certified that error appears in the above-identified patent and that said Letters Patent is hereby corrected as shown below:

Title Pg, Item (56), Column 2 (Other Publications), line 35, delete "on" and insert -- of --;

Title Pg, Item (56), Column 2 (Other Publications), line 36, delete "Netrophil" and insert -- Neutrophil --;

Title Pg, item (57), Column 2 (Abstract), line 5, delete "manner." and insert -- manner, as well as fragments and variants thereof. --.

Signed and Sealed this
Sixth Day of December, 2011

David J. Kappos
*Director of the United States Patent and Trademark Office*